US012702498B2

(12) United States Patent
Hourtash et al.

(10) Patent No.: US 12,702,498 B2
(45) Date of Patent: Aug. 11, 2026

(54) METHOD AND SYSTEM FOR CONTROLLING INSTRUMENT GRIP BEHAVIOR

(71) Applicant: Intuitive Surgical Operations, Inc., Sunnyvale, CA (US)

(72) Inventors: Arjang M. Hourtash, East Palo Alto, CA (US); Christine E. Draper, Menlo Park, CA (US); Caroline A. Edwards, Foster City, CA (US); Michael Ikeda, Sunnyvale, CA (US); Erasmo Lopez Calleros, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 944 days.

(21) Appl. No.: 17/763,180

(22) PCT Filed: Sep. 24, 2019

(86) PCT No.: PCT/US2019/052693

§ 371 (c)(1),
(2) Date: Mar. 23, 2022

(87) PCT Pub. No.: WO2021/061105

PCT Pub. Date: Apr. 1, 2021

(65) Prior Publication Data

US 2022/0331025 A1 Oct. 20, 2022

(51) Int. Cl.

*A61B 34/30* (2016.01)
*A61B 17/29* (2006.01)
*A61B 34/20* (2016.01)

(52) U.S. Cl.

CPC .............. *A61B 34/30* (2016.02); *A61B 17/29* (2013.01); *A61B 2034/2059* (2016.02); *A61B 2034/305* (2016.02)

(58) Field of Classification Search

CPC . A61B 34/30; A61B 17/29; A61B 2034/2059; A61B 2034/305

See application file for complete search history.

(56) References Cited

U.S. PATENT DOCUMENTS 8,620,473 B2 12/2013 Diolaiti et al.
8,903,546 B2 12/2014 Diolaiti et al.

(Continued)

FOREIGN PATENT DOCUMENTS

CN 108430350 A 8/2018
CN 110191690 A 8/2019

(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

(Continued)

*Primary Examiner* — Mohamed G Gabr
*Assistant Examiner* — Khoa Tan Le
(74) *Attorney, Agent, or Firm* — Osha Bergman Watanabe & Burton LLP

(57) ABSTRACT

A computer-assisted medical system includes a robotic manipulator arm configured to support an instrument. The instrument includes an instrument shaft and jaws disposed at a distal end of the instrument shaft. The computer-assisted medical system further includes a controller coupled to the manipulator arm. The controller includes a computer processor and is configured to track a movement of the instrument along an insertion axis of the instrument, and coordinate a size of a jaw aperture defined by the jaws with the movement of the instrument along the insertion axis to reach a target aperture.

28 Claims, 10 Drawing Sheets

(56) References Cited

U.S. PATENT DOCUMENTS

| | | | | |
|---|---|---|---|---|
| 9,084,623 | B2 | 7/2015 | Gomez et al. | |
| 9,138,129 | B2 | 9/2015 | Diolaiti | |
| 9,386,983 | B2 * | 7/2016 | Swensgard | A61B 34/30 |
| 9,586,323 | B2 | 3/2017 | Diolaiti et al. | |
| 2004/0193197 | A1 | 9/2004 | Vidal | |
| 2007/0013336 | A1 * | 1/2007 | Nowlin | A61B 34/30 318/568.21 |
| 2011/0040305 | A1 * | 2/2011 | Gomez | A61B 34/74 606/130 |
| 2011/0125165 | A1 * | 5/2011 | Simaan | A61F 9/007 29/428 |
| 2011/0152892 | A1 | 6/2011 | Saliman | |
| 2013/0193189 | A1 | 8/2013 | Swensgard et al. | |
| 2014/0246479 | A1 * | 9/2014 | Baber | A61B 90/90 227/180.1 |
| 2016/0220320 | A1 | 8/2016 | Crawford et al. | |
| 2018/0064493 | A1 * | 3/2018 | Cooper | A61B 34/35 |
| 2018/0250084 | A1 * | 9/2018 | Kopp | A61B 17/3421 |
| 2019/0000568 | A1 | 1/2019 | Connolly et al. | |
| 2019/0159778 | A1 | 5/2019 | Shelton, IV et al. | |
| 2021/0401515 | A1 | 12/2021 | Rockrohr et al. | |

FOREIGN PATENT DOCUMENTS

| | | | |
|---|---|---|---|
| EP | 3873371 | A1 | 9/2021 |
| JP | 2007244437 | A | 9/2007 |
| WO | WO-2013071057 | A1 | 5/2013 |
| WO | WO-2013071071 | A1 | 5/2013 |
| WO | 2014078388 | A1 | 5/2014 |
| WO | WO-2018005928 | A1 | 1/2018 |
| WO | WO-2020092312 | A1 | 5/2020 |
| WO | WO-2021061105 | A1 | 4/2021 |

OTHER PUBLICATIONS

International Search Report issued in corresponding international application No. PCT/US2019/052693 mailed Jun. 23, 2020 (4 pages).

Written Opinion of the International Searching Authority issued in corresponding international application No. PCT/US2019/052693 mailed Jun. 23, 2020 (3 pages).

Extended European Search Report for Application No. EP19946646.7, mailed on Sep. 1, 2022 10 pages.

* cited by examiner

METHOD AND SYSTEM FOR CONTROLLING INSTRUMENT GRIP BEHAVIOR

CROSS-REFERENCE TO RELATED APPLICATION

This application is a national stage filing under 35 U.S.C. § 371 of International Patent Application Serial No. PCT/US2019/052693, filed Sep. 24, 2019, which is incorporated herein by reference in its entirety.

BACKGROUND

Field of Invention

The present invention generally provides improved robotic and/or medical (including surgical) devices, systems, and methods.

Overview

A system of robotic devices can be used to perform a task at a worksite. For example, robotic systems may include robotic manipulators to manipulate instruments for performing the task. A robotic manipulator may include two or more links coupled together by one or more joints. The joints may be active joints that are actively moved and controlled. The joints may also be passive joints that comply with movement of the active joints or with external manipulation. Such active and passive joints may be, for example, revolute or prismatic joints. The configuration of the robotic manipulator and the instrument attached to the robotic manipulator may then be determined by the positions and orientations of the joints of the robotic manipulator, and by the structure of the robotic manipulator such as the design of the links of the robotic manipulator.

Example robotic systems include industrial and recreational robotic systems. Example robotic systems also include medical robotic systems used in procedures for diagnosis, non-surgical treatment, surgical treatment, etc. As a specific example, robotic systems include minimally invasive, robotic telesurgical systems in which a surgeon may operate on a patient from bedside or a remote location. Telesurgery refers generally to surgery performed using surgical systems where the surgeon uses some form of remote control, e.g., a servomechanism, to manipulate surgical instrument movements rather than directly holding and moving the instruments by hand. A robotic medical system usable for telesurgery or other telemedical procedures may include a remotely controllable robotic manipulator. Operators may remotely control motion of the remotely controllable robotic manipulator. Operators may also manually move pieces of the robotic medical system into positions or orientations within its environment.

An instrument may be inserted into or withdrawn from a worksite. Consider, for example, a scenario in which a robotic system is used to perform a surgery. A typical surgery employs a number of different surgical instruments. The instruments may have various end effectors. At least some of these instruments may be equipped with end effectors that have jaws configured to open and close. Such instruments may be, for example, forceps, scissors, needle drivers, clip appliers, etc. The jaws of an instrument may be in an opened or closed position, or in an intermediate position.

For these and other reasons, it would be advantageous to provide improved devices, systems, and methods for robotic applications, including industrial, recreational, medical, and other robotic applications.

SUMMARY

In general, in one aspect, one or more embodiments relate to a computer-assisted medical system comprising a robotic manipulator arm configured to support an instrument, the instrument comprising an instrument shaft, and jaws disposed at a distal end of the instrument shaft; and a controller coupled to the manipulator arm, the controller comprising a computer processor and configured to: track a movement of the instrument along an insertion axis of the instrument, and coordinate a size of a jaw aperture defined by the jaws with the movement of the instrument along the insertion axis to reach a target aperture.

In general, in one aspect, one or more embodiments relate to a method for operating a medical system, comprising: tracking a movement of an instrument along an insertion axis of the instrument, wherein the instrument comprises an instrument shaft and jaws disposed at a distal end of the instrument shaft; and coordinating a size of a jaw aperture defined by the jaws with the movement of the instrument along the insertion axis to reach a target aperture.

In general, in one aspect, one or more embodiments relate to non-transitory machine-readable medium comprising a plurality of machine-readable instructions executed by one or more processors associated with a medical system, the plurality of machine-readable instructions causing the one or more processors to perform a method comprising: tracking a movement of an instrument along an insertion axis of the instrument, wherein the instrument comprises an instrument shaft and jaws disposed at a distal end of the instrument shaft; and coordinating a size of a jaw aperture defined by the jaws with the movement of the instrument along the insertion axis to reach a target aperture.

Other aspects of the invention will be apparent from the following description and the appended claims.

DETAILED DESCRIPTION

Figure 1:
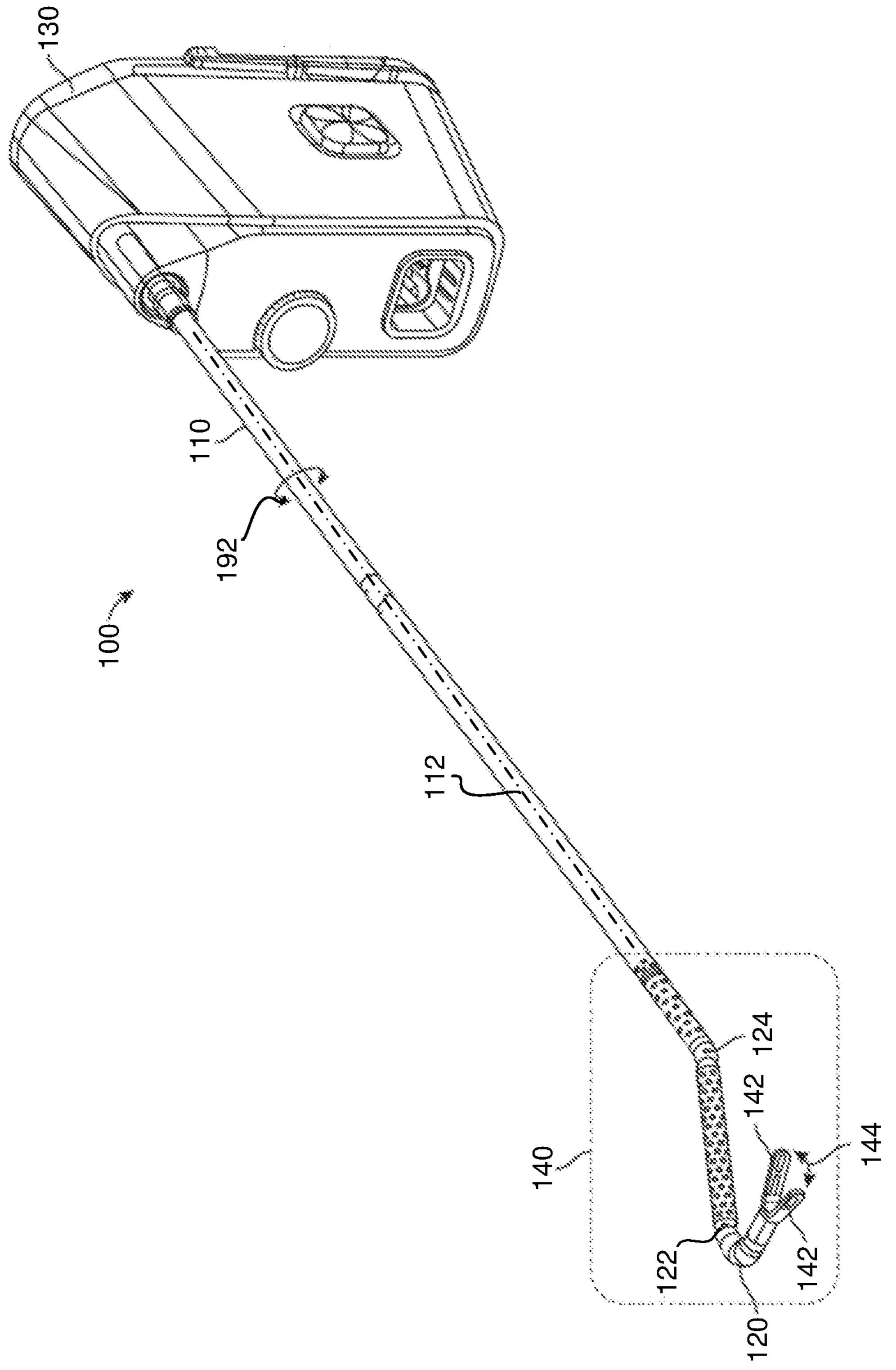
FIG. 1 shows an example of an instrument in accordance with one or more embodiments.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Although some of the examples described herein refer to surgical procedures or tools, or medical procedures and medical tools, the techniques disclosed apply to medical and non-medical procedures, and to medical and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for medical treatment or diagnosis procedures that do, or do not, include surgical aspects.

In general, embodiments of the disclosure may support the insertion and retraction of an instrument or tool during a robotic procedure (e.g. a medical procedure such as a robotic surgical procedure) by adjusting an aperture of the instrument jaws (also "jaw aperture") during the insertion/retraction. Depending on the environment at the worksite, it may be preferable to adjust the jaws of an instrument to a certain configuration when inserting or withdrawing the instrument. In one example, when an instrument is to be withdrawn from the worksite, the instrument may be grasping tissue when in a grasping configuration (with the jaws closed or mostly closed). Withdrawing the instrument from the worksite when in the grasping configuration may unintentionally expose the grasped tissue to a tugging force. It may, thus, be desirable to open the jaws prior to the retraction of the instrument. In another example, the jaws of an instrument to be inserted or withdrawn may be wide-open, thus increasing the possibility of a collision (e.g., with other instruments or tissue) when moving the instrument. In this case, it may be preferable to close the jaws prior to moving the instrument for insertion or retraction. In one or more embodiments, instrument jaws that are initially in a grasping configuration are opened to some extent to reach a target aperture during a retraction of the instrument. In one or more embodiments, instrument jaws that are initially in an open configuration are closed to some extent to reach a target aperture during an insertion or retraction of the instrument.

Embodiments of the disclosure may enable a straightforward and efficient insertion and/or retraction of instruments during robotic procedures. In the example of robotic surgeries, embodiments of the disclosure may reduce the likeliness of unintended interaction of an instrument being inserted or retracted with tissue and/or adjacent instruments. Additional features are discussed in the following description.

Referring now to the drawings, in which like reference numerals represent like parts throughout the several views, FIG. 1 shows an example of an instrument (100) (also called tool (100)) as it may be used for robotic procedures such as robotic surgeries, in accordance with one or more embodiments. The instrument (100) includes an elongate shaft (110) and at least one joint located at a working end of the shaft (110). In the FIG. 1 example, the at least one joint includes a wrist (120) proximal to the end effector (140) and two joints (122, 124) proximal to the wrist. A housing (130), arranged releasably to couple the instrument (100) to a manipulator arm (shown, for example, in FIG. 2), is located at an opposed end of the shaft (110). The shaft (110) may be rotatably coupled to the housing (130) to enable angular displacement of the shaft (110) relative to the housing (130) as indicated by arrows (192) thereby allowing a rotation of the end effector (140) coupled to the shaft via the wrist (120).

Figure 2:
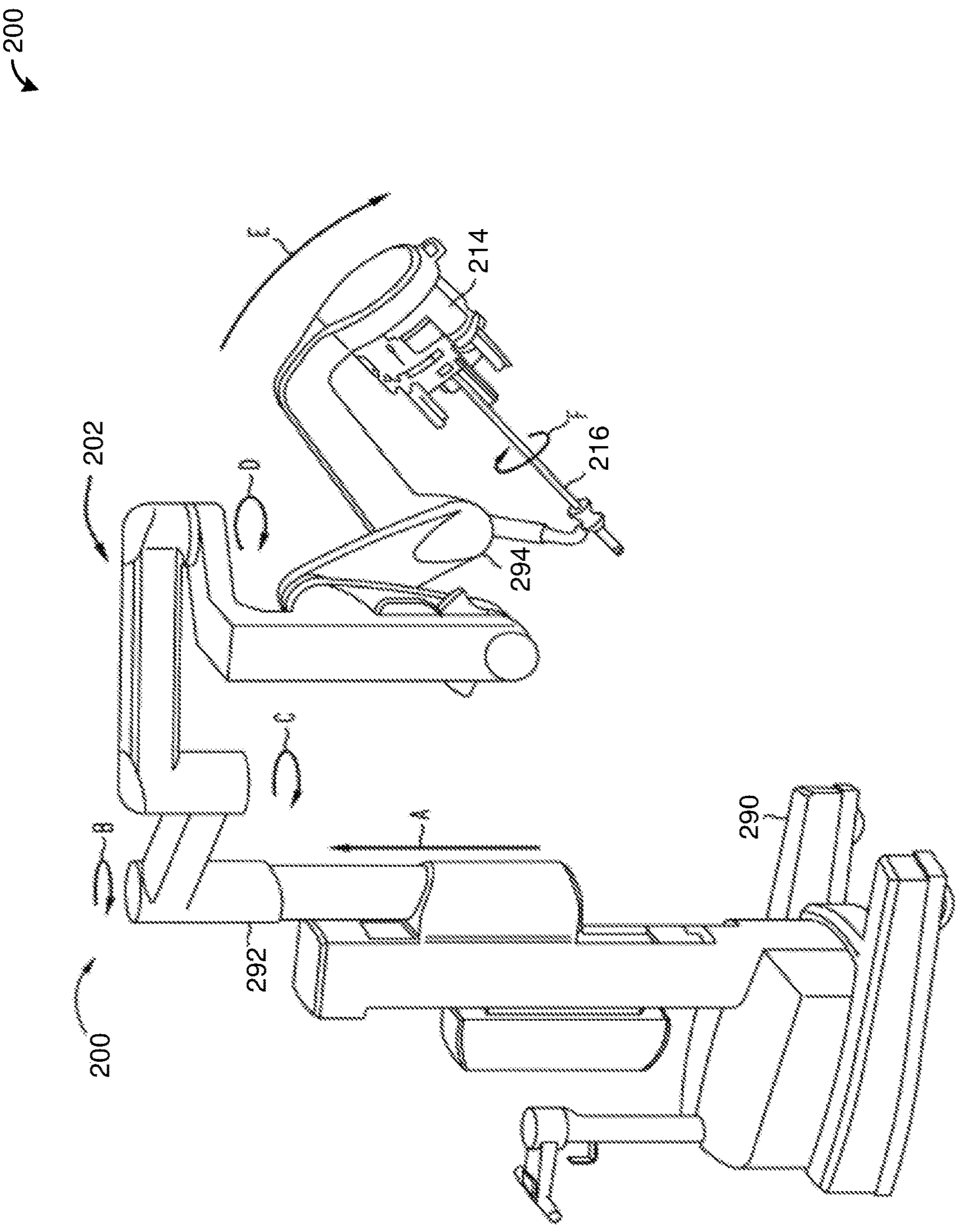
FIG. 2 shows an example of a manipulator assembly including an instrument and a manipulator arm holding the instrument, in accordance with one or more embodiments.

The instrument (100) typically is releasably mounted on an instrument holder of the manipulator arm (as shown in FIG. 2), which may be driven to translate along a linear guide. Accordingly, the instrument may have an insertion degree of freedom for an insertion/retraction of the instrument (100) along the insertion axis (112).

Various types of end effectors (140), further described below, exist. For example, the end effector (140) may include jaws (142) that may open and close, defining an aperture (144) (also "jaw aperture"). The end effector may be actuated by control cables that connect the end effector to cable drive elements (e.g. pulleys, capstans, spools, or the like) (not shown) in the housing (130). Rotation of the cable drive elements may thus control the end effector, such that the end effector may pivot, the jaws may open and close, etc.

Upon mounting of the instrument (100) on a manipulator arm, the cable drive elements may engage with actuators of the manipulator arm. Other degrees of freedom of the instrument (100) may be controlled in a similar manner. A description of the control of the instrument (100) may be found in U.S. Pat. No. 6,394,998, entitled "Surgical Tools for Use in Minimally Invasive Telesurgical Applications." Further, a more detailed description of the end effector (140) is provided below, with reference to FIG. 4A and FIG. 4B. Other instruments (100) may enable control the motion of the end effector through other appropriate mechanisms, such as by use of metal bands, drive screws, linkages, tubes, push rods, etc., and such mechanisms can similarly be driven by actuators of the manipulator arm.

While FIG. 1 shows a particular configuration of an instrument, designed to engage with a particular type of manipulator arm, other configurations of instruments are within the scope of the disclosure. For example, embodiments of instrument (100) may have multi-degree-of-freedom wrists (e.g., pitch and yaw degrees of freedom), single-degree-of-freedom wrists (e.g., pitch or jaw), or no wrists. Further, different housings (130) may be used to interface with different types of manipulator arms.

Turning to FIG. 2, an example of a manipulator assembly (200), in accordance with one or more embodiments, is shown. The manipulator assembly (200) may be used to introduce a plurality of articulated instruments to a work site through a single entry aperture in the patient through a cannula (216). The aperture may be a minimally invasive incision or a natural body orifice. The cannula (216) may be a cylindrical structure which is held and manipulated by a manipulator arm (202), which may be mounted on a base (290). The manipulator arm may include a setup arm (292) and an entry guide manipulator (294). The setup arm (292) includes a set of links and joints which may be used to position the cannula (216) at the aperture. In the example shown in FIG. 2, the setup arm (292) includes a prismatic joint for adjusting the height of the setup arm (292) (as indicated by arrow "A") and a set of rotary joints for adjusting the horizontal position of the setup arm (292) (as indicated by arrows "B" and "C"). The entry guide manipulator (294) is used to robotically pivot the cannula (216) (and the articulated instruments disposed within it at the time) in yaw, pitch and roll angular rotations about the pivot point as indicated by arrows D, E and F, respectively.

Actuation of the degrees of freedom of the instrument may be provided by actuators disposed in, or that transmit force or torque to, the carriage (214). As previously noted, the actuators may drive disks that couple with cable drive elements (or other drive elements) of the instrument to drive the cables (or other end effector control mechanisms) upon connection of the instrument to the manipulator arm (202). Accordingly, the degrees of freedom of the instrument may be controlled by actuators, e.g., electrical motors, which respond to inputs from the associated input control devices (e.g. input control devices of the user control system (320) in FIG. 3) to drive the instrument as dictated by movement of the input control devices or any other control signal. Furthermore, appropriately positioned sensors, e.g., encoders, potentiometers, etc., may be provided to enable measurement of the joint positions. The actuators and sensors may be disposed in, or transmit to or receive signals from, the carriage (214).

While the manipulator assembly (200) shows a particular manipulator arm (202), those skilled in the art will appreciate that embodiments of the disclosure may be used with any type of manipulator arm. For example, a manipulator arm may have any number and any types of degrees of freedom, may or may not include a cannula as shown in FIG. 2, etc.

Figure 3:
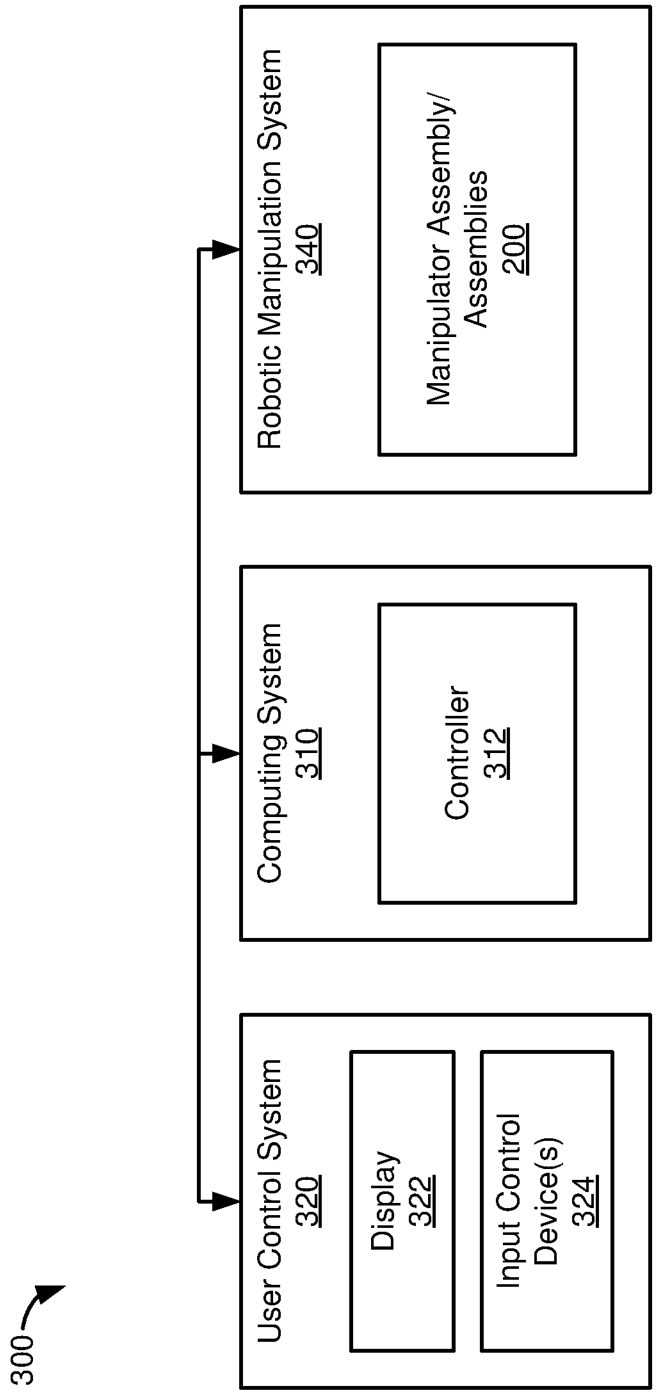
FIG. 3 diagrammatically shows a computer-assisted medical system, in accordance with one or more embodiments.

FIG. 3 diagrammatically shows a computer-assisted medical system (300), in accordance with one or more embodiments. The system (300) may include one or more computing systems (310), a user control system (320), and a robotic manipulation system (340). Each of these components is subsequently described.

The robotic manipulation system (340) may be a system that includes at least one manipulator arm configured to support at least one instrument and form at least one manipulator assembly (200), as shown in FIG. 2. Frequently, the robotic manipulation system (340) includes multiple such manipulator assemblies. The robotic manipulation system (340) may receive control signals from the user control system (320) and/or the computing system (310) and may return feedback (e.g., positional encoder data from joint sensors, image data from image tools such as endoscopes, etc.).

The user control system (320) may include components enabling an operator to operate the robotic manipulation system (340). The user control system (320) may include a display system (322) for presenting the operator with a view of the worksite with which the robotic manipulation system interacts. The view may include coordinated stereoscopic images to provide a depth perception of the worksite and the instrument(s) of the robotic manipulation system (340) in the worksite. The user control system (320) may further include one or more input control devices (324), which may be used by the operator to operate one or more instruments of the robotic manipulation system (340). The input control devices may be any type of device manually operable by human user, e.g., joysticks, trackballs, and/or other types of haptic devices typically equipped with multiple degrees of freedom. The input control devices (324) may provide the same degrees of freedom as their associated instruments so as to provide the operator with telepresence, or the perception that the input control devices (324) are integral with the instruments (160) so that the operator has a strong sense of directly controlling the instruments. To this end, position, force, and/or tactile feedback sensors (not shown) may be employed to transmit position, force, and/or tactile sensations from the instruments back to the operator's hands through the input control devices (324).

The computing system (310) may be used to process input provided by the user control system (320) from the operator. The computing system may further be used to provide an output, e.g., a video image to the display (330). One or more computing systems (310) may further be used to control the robotic manipulating system (340).

In one or more embodiments, the computing system (310) executes a controller (312). The controller (312) may include instructions that implement methods for controlling one or more components of the robotic manipulation system (340) including one or more of the manipulator assemblies (200). In one or more embodiments, the joint movements of the manipulator assembly are controlled by driving one or more joints by the controller (312) using actuators (e.g. motors, solenoids, etc.) of the manipulator assembly, the joint movements being calculated by a processor of the controller. Mathematically, the controller (312) may perform at least some of the calculations of the joint commands using vectors and/or matrices, some of which may have elements corresponding to positions, velocities, and/or forces/torques of the joints. The range of alternative joint configurations available to the controller (312) may be conceptualized as a joint space. The joint space may, for example, have as many dimensions as the manipulator assembly has degrees of freedom, and a particular configuration of the manipulator assembly may represent a particular point in the joint space, with each coordinate corresponding to a joint state of an associated joint of the manipulator assembly.

As used herein, the term "state" of a joint or multiple joints refers to the control variables associated with the joint or the multiple joints, respectively. For example, the state of an angular joint may refer to the angle defined by that joint within its range of motion, and/or to the angular velocity of the joint. Similarly, the state of an axial or prismatic joint may refer to the joint's axial position, and/or to its axial velocity. While one or more of the controllers (312) described herein include position controllers, they often also have velocity control aspects. Alternative embodiments may rely primarily or entirely on velocity controllers, force controllers, acceleration controllers, etc. without departing from the disclosure. Many aspects of control systems that may be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, etc.

Additional control modes may further exist. For example, during a robotic task being performed under the control of input control devices (324) operated by a user, various joints of the robotic manipulator assembly may be position-controlled. However, in another control mode, one or more of the joints may be "floating", allowing an assistant to readily externally articulate these one or more joints, such as by back-driving these one or more joints. A floating joint may be back-driven by an externally applied force without a control algorithm or a braking force counteracting sufficient externally applied force. For example, a user may apply a force meeting one or more criteria (e.g., for magnitude, direction, duration, frequency) to a link distal to the floating joint, causing the back-driving of the floating joint. A floating joint, in particular when floating in a degree of freedom affected by gravity (e.g. a "vertical" joint or in a "non-horizontal" direction), may further be gravity-compensated. In addition, a friction compensation may facilitate the back-driving. Additionally or alternatively, a floating joint may also be controlled to impose other characteristics such as a certain level of damping. Multiple control modes may be combined during operation of the manipulator assembly, e.g., some joints may be position controlled to resist or rebound from external articulation of those joints, while other joints may be floating and facilitate external articulation of those other joints. In addition, one or more joints of the manipulator assembly may be passive, i.e., not position or velocity controlled at all. Passive joints may be manually operated by an assistant. Passive joints may, nevertheless, include joint sensors such that the full kinematics of the manipulator assembly may be obtained. Further, in some embodiments, passive joints may contain actuators for supplying gravity compensation, friction compensation, or other utility not including actively driving the motion of the passive joint.

The architecture of the controller (312) used for controlling the robotic manipulation system may be hierarchical and may include a high-level controller and multiple joint controllers. A commanded movement may be received by the high-level controller in, for example, a Cartesian-coordinate space (referred to herein as Cartesian-space). The commanded movement may be, for example, a movement command (e.g., in the form of a position and/or velocity) received from the user control system (320), or any other movement command. The commanded movement may then be converted into commanded joint positions (e.g., joint angles for rotary joints). The conversion may be performed by an inverse kinematics algorithm. Subsequently, the joint controllers may convert the received commanded joint positions into commanded currents to drive the joint actuators producing joint movements. The joint movements of all joint actuators through the kinematics of the manipulator assembly may produce a manipulator assembly movement that reflects the commanded movement. In one embodiment of the disclosure, a joint controller controls a joint position or angle. Alternatively, the joint controller may control other variables such as joint velocity, joint torque or joint force (in case of a linear joint). A joint controller may receive a feedback signal in the form of a sensed joint state from the associated joint actuator to enable closed-loop control. The sensed joint state provided by the joint actuator may include a joint position, a joint velocity, and/or a joint acceleration, etc., representing the joint movement. The sensed joint state may be derived from signals obtained from a sensor attached to the joint. Such a sensor may be, for example, an incremental encoder or a hall sensor of the joint actuator. A state observer or estimator (not shown) may be used. Each joint controller (750) may implement a proportional integral derivative (PID), proportional derivative (PD), full state feedback, sliding mode, or various other control schemes, without departing from the disclosure.

Figure 6:
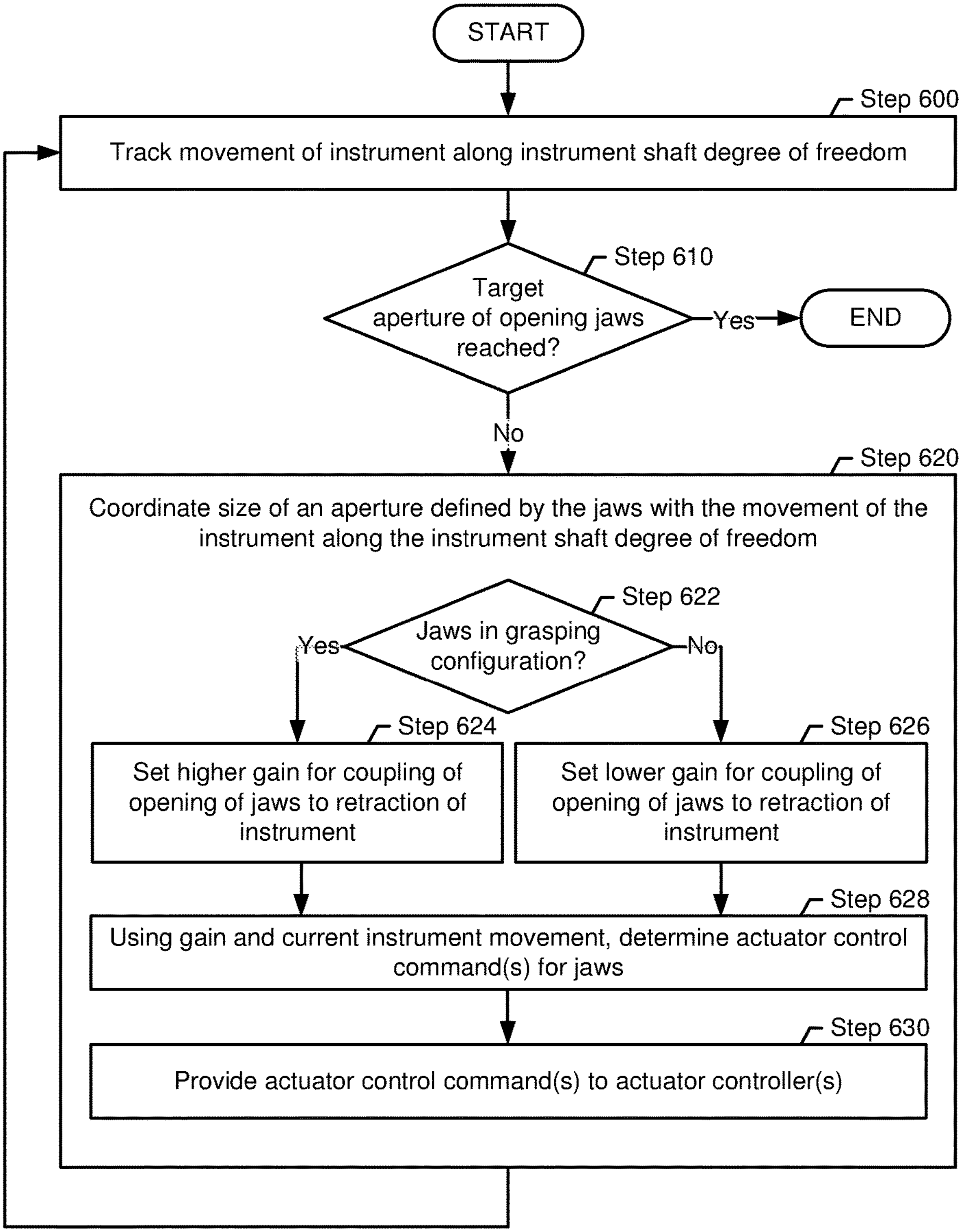
FIG. 6 shows a flowchart describing a method for controlling instrument grip behavior when retracting an instrument with the instrument's jaws initially in a grasping configuration, in accordance with one or more embodiments.
Figure 7:
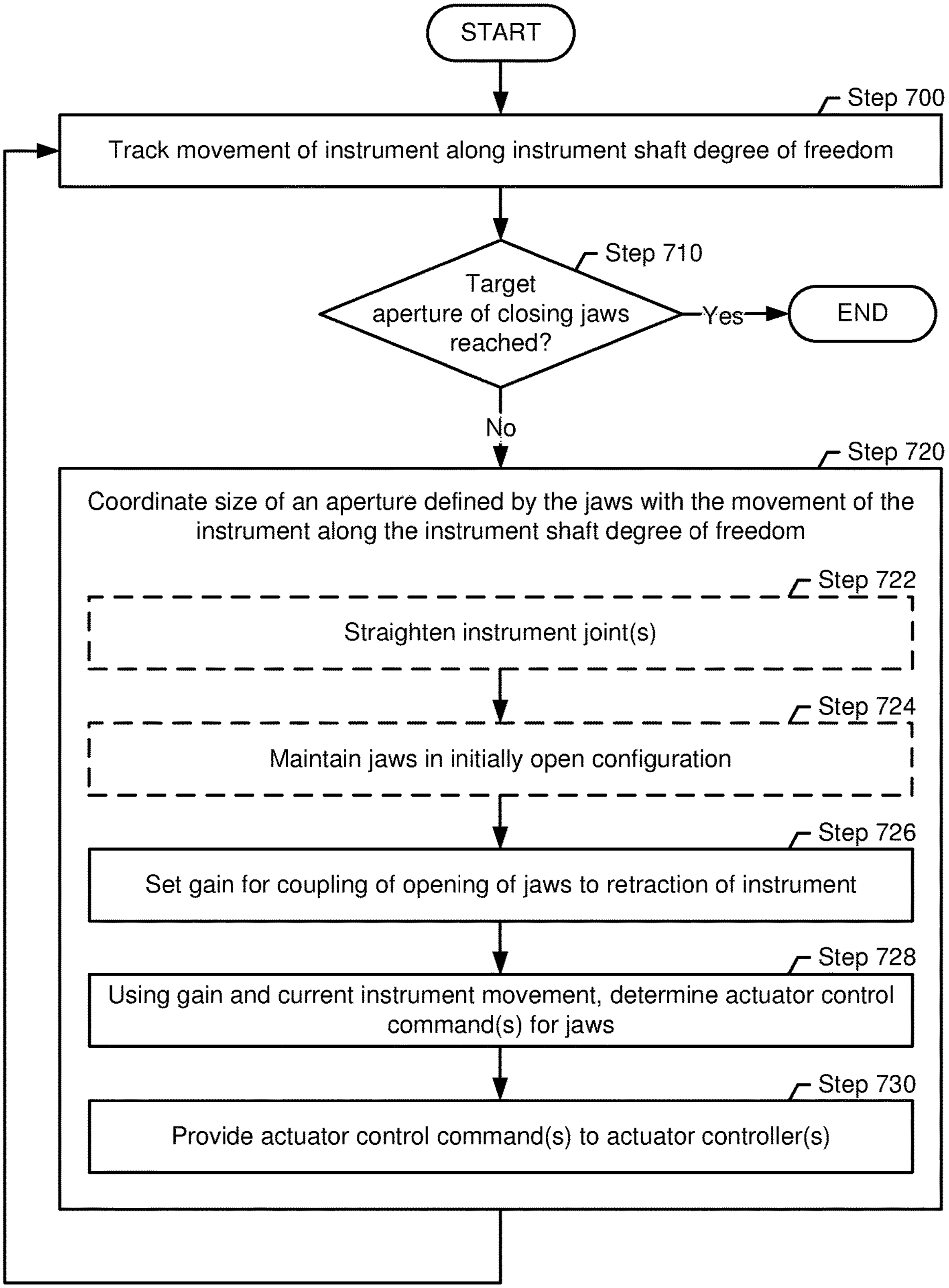
FIG. 7 shows a flowchart describing a method for controlling instrument grip behavior when retracting an instrument with the instrument's jaws initially in an open configuration, in accordance with one or more embodiments.
Figure 8:
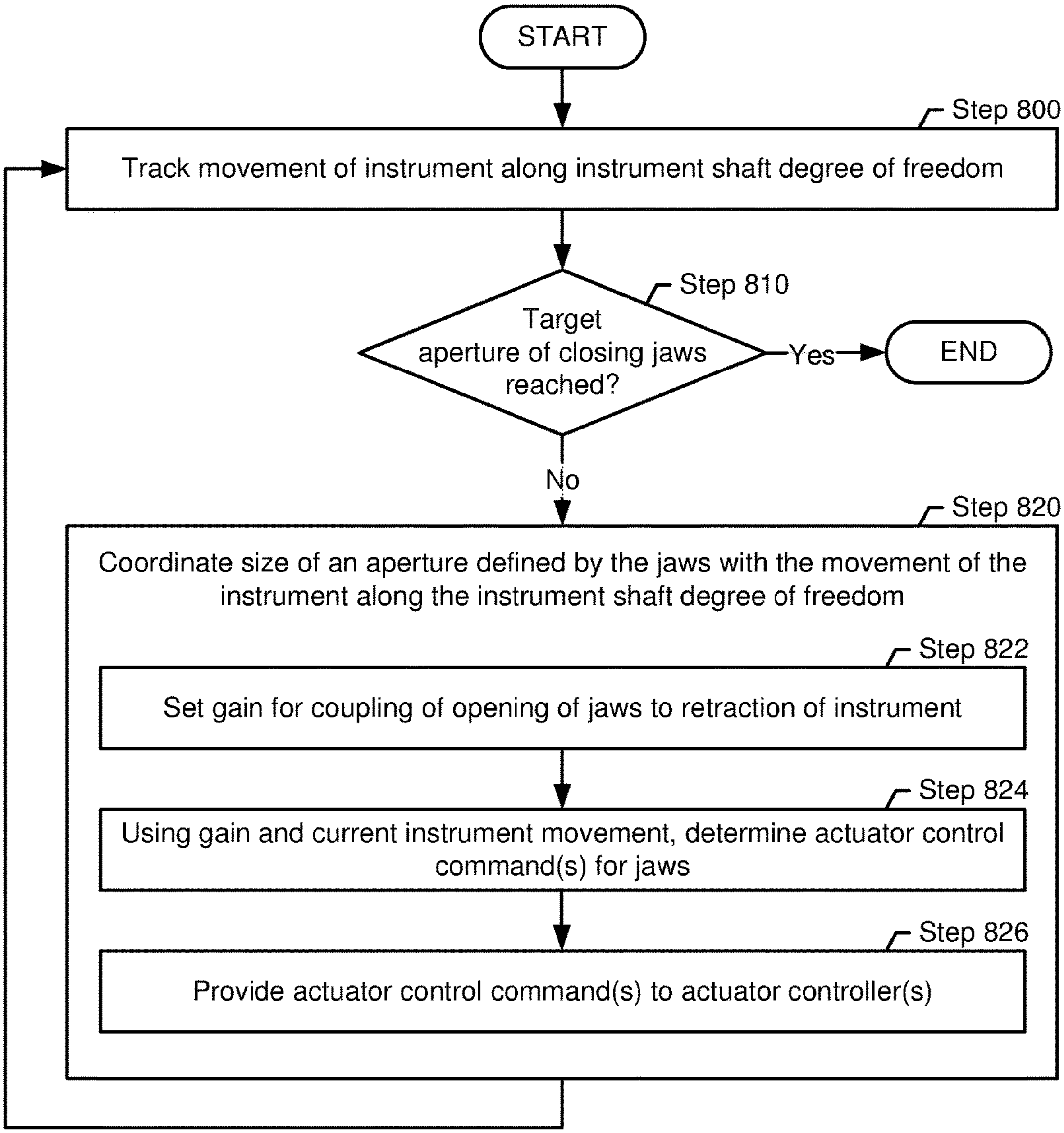
FIG. 8 shows a flowchart describing a method for controlling instrument grip behavior when inserting an instrument with the instrument's jaws initially in an open configuration, in accordance with one or more embodiments.

In one or more embodiments, the controller (312) is further configured to perform at least one of the steps described in FIGS. 6, 7, and 8 which may be used to drive one or more of the actuators of the manipulator assembly (200).

The computing system (310) may include one or more computer processors, non-persistent storage (e.g., volatile memory, such as random access memory (RAM), cache memory), persistent storage (e.g., a hard disk, an optical drive such as a compact disk (CD) drive or digital versatile disk (DVD) drive, a flash memory, etc.), a communication interface (e.g., Bluetooth interface, infrared interface, network interface, optical interface, etc.), and numerous other elements and functionalities.

A computer processor of a computing system (310) may be an integrated circuit for processing instructions. For example, the computer processor may be one or more cores or micro-cores of a processor. The computing system (310) may also include one or more input devices, such as a touchscreen, keyboard, mouse, microphone, touchpad, electronic pen, or any other type of input device.

A communication interface of a computing system (310) may include an integrated circuit for connecting the computing system (310) to a network (not shown) (e.g., a local area network (LAN), a wide area network (WAN) such as the Internet, mobile network, or any other type of network) and/or to another device, such as another computing system (310).

Further, the computing system (310) may include one or more output devices (not shown), such as a display device (e.g., a liquid crystal display (LCD), a plasma display, touchscreen, organic LED display (OLED), projector, or other display device), a printer, a speaker, external storage, or any other output device. One or more of the output devices may be the same or different from the input device(s). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

A computing system (310) may be connected to or be a part of a network. The network may include multiple nodes. Each node may correspond to a computing system, or a group of nodes. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system may be located at a remote location and connected to the other elements over a network.

While FIG. 1, FIG. 2, and FIG. 3 show various configurations of components, other configurations may be used without departing from the scope of the disclosure. For example, various components may be combined to create a single component. As another example, the functionality performed by a single component may be performed by two or more components. Further, while the components are described in context of surgical scenarios, embodiments of the disclosure may be equally applicable to other domains that involve robotic manipulation, e.g., non-surgical scenarios or systems, non-medical scenarios or systems.

Figure 4B:
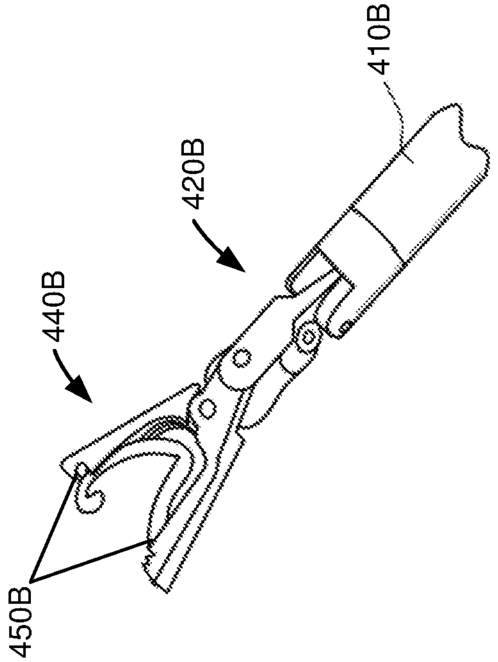
FIG. 4A and FIG. 4B show examples of end effectors of instruments, in accordance with one or more embodiments.
Figure 4A:
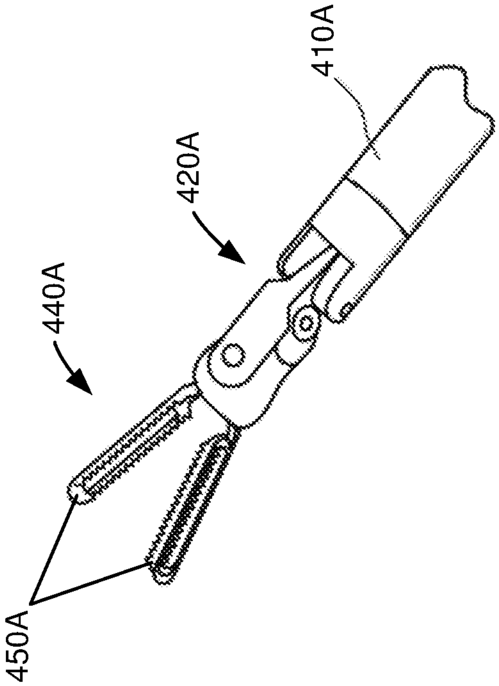

Turning to FIG. 4A and FIG. 4B, examples of end effectors of instruments, in accordance with one or more embodiments, are shown. Each instrument (400A, 400B) shown in FIG. 4A and FIG. 4B comprises a wrist (420A, 420B) disposed on a working end of its shaft (410A, 410B). The wrist (420A, 420B) may enable a pivoting of the end effector (440A, 440B) relative to the shaft (410A, 410B). The wrist (420A, 420B) may have at least one degree of freedom.

Different types of instruments (400A, 400B) may have different end effectors with different geometries, degrees of freedom, and/or functions. For example, the end effector (440A) in FIG. 4A includes two members or jaws (450A) forming forceps, and the end effector (440B) in FIG. 4B is a clip applier formed by jaws (450B). In one or more embodiments, the end effector (440A, 440B) may be in the form of any desired instrument, e.g., having two or more jaws which pivot relative to each other. "Jaws" is used herein to refer to any fingers or other end effector members that move relative to each other. Such instruments may be, for example, scissors, two-fingered blunt dissection instruments, forceps (as shown in FIG. 4A), needle drivers or other plier-like instruments, clip appliers for anchoring clips (as shown in FIG. 4B), or the like. Both members (450A, 450B) of the end effector (440A and 440B) may be individually angularly displaceable, thereby not only allowing an opening and closing of the end effector, but also enabling an angular displacement to change the orientation of the end effector (440A, 440B) as a whole, relative to the wrist (420A, 420B).

Figures 5A, 5B:
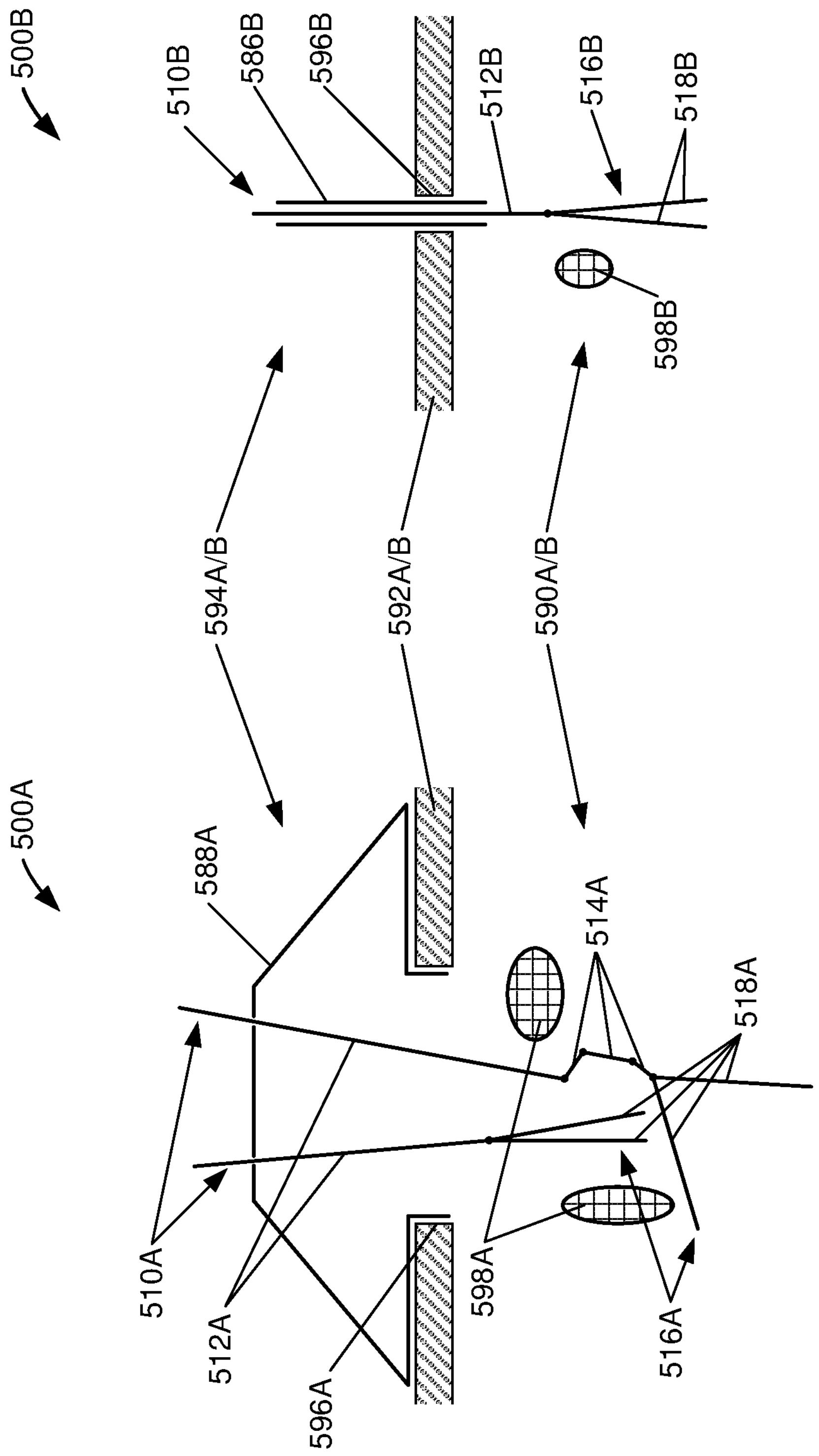
FIG. 5A and FIG. 5B schematically show examples of instruments in worksites, in accordance with one or more embodiments.

Turning to FIG. 5A and FIG. 5B, examples (500A, 500B) of instruments in worksites, in accordance with one or more embodiments, are shown. In minimally invasive scenarios, the instruments (510A, 510B) may be positioned and manipulated through incisions in the patient so that a kinematic remote center is maintained at the incision so as to minimize the size of the incision or forces applied to tissue surrounding the incision. The incision may form an access port (596A, 596B) through a wall (592A, 592B), for example, an abdominal wall, providing access to the worksite (590A, 590B) from an external environment (594A, 594B). In the example (500A) of FIG. 5A, a larger size access port (596A) enables the simultaneous insertion of multiple instruments (510A). The access port may be sealed by an access port seal (588A). The access port seal (588) may provide a gas-tight seal, allowing insufflation of the cavity in which the worksite (590A) is located, e.g., the abdomen of a patient. In contrast in the example (500B) of FIG. 5B, a smaller size access port (596B) accommodates a cannula (586B) through which a single instrument (510B) may be inserted. The cannula (586B), similar to the access port seal (588A), may provide a gas-tight seal, separating the external environment (594A, 594B) from the worksite (590A, 590B).

In one or more embodiments, an instrument (510A, 510B) is equipped with an end effector (516A, 516B) disposed on a distal end of an instrument shaft (512A, 512B). The end effector may include at least two jaws (518A, 518B). Such end effectors (516A, 516B) may be designed to interact with objects (598A, 598B) in the worksite (590A, 590B). For example, the end effectors (516A, 516B) may be scissors, forceps, staplers, etc. While the end effectors (516A, 516B) may interact with the objects (598A, 598B) in certain situations, in other situations it may be desirable to avoid an interaction of the end effectors (516A, 516B) with the objects (598A, 598B). In particular, when inserting or retracting an instrument (510A, 510B), it may be desirable to avoid interaction with an object (598A, 598B) thereby avoiding unintentional manipulation of the object. Similarly, one may also want to avoid an interaction (i.e., touch) between two instruments (510A, 510B). To avoid such interaction, the configuration of the jaws of an instrument may be adjusted. For example, the jaws (518A, 518B) may be opened or closed to a certain extent. A detailed description of an adjustment of the configuration of the jaws (518A, 518B) during an insertion or retraction of an instrument (510A, 510B) is provided below with reference to the subsequently discussed figures. Those skilled in the art will appreciate that instruments (510A, 510B) in accordance with embodiments of the disclosure may have various configurations. For example, an instrument may have additional degrees of freedom, as shown in FIG. 5A, in which the instrument shaft (512A) includes additional shaft segments (514A) to enable additional articulation.

FIG. 6, FIG. 7, and FIG. 8 show flowcharts in accordance with one or more embodiments. The flowcharts of FIG. 6, FIG. 7, and FIG. 8 depict methods for controlling instrument grip behavior when retracting or inserting an instrument, in accordance with one or more embodiments. More specifically the methods coordinate an aperture defined by the jaws (a "jaw aperture") of an instrument with the insertion or retraction of the instrument. One or more of the steps in FIG. 6, FIG. 7, and FIG. 8 may be performed by various components of the systems, previously described with reference to FIG. 1, FIG. 2, FIG. 3, FIG. 4A, FIG. 4B, FIG. 5A, and FIG. 5B. These figures describe particular instruments and manipulator arms and particular tools, the manipulator arms and tools having certain configurations. However, the subsequently described methods are not limited to a particular configuration of manipulator arms, instruments and/or degrees of freedom. Instead, the methods are applicable to any type of instrument equipped with jaws, paired with any type of manipulator arm, used in any type of scenario.

While the various steps in these flowcharts are presented and described sequentially, one of ordinary skill will appreciate that some or all of the steps may be executed in different orders, may be combined or omitted, and some or all of the steps may be executed in parallel. Additional steps may further be performed. Furthermore, the steps may be performed actively or passively. For example, some steps may be performed using polling or be interrupt driven in accordance with one or more embodiments of the disclosure. By way of an example, determination steps may not require a processor to process an instruction unless an interrupt is received to signify that condition exists in accordance with one or more embodiments of the disclosure. As another example, determination steps may be performed by performing a test, such as checking a data value to test whether the value is consistent with the tested condition in accordance with one or more embodiments of the disclosure. Accordingly, the scope of the disclosure should not be considered limited to the specific arrangement of steps shown in FIG. 6, FIG. 7, and FIG. 8.

Figure 9A:
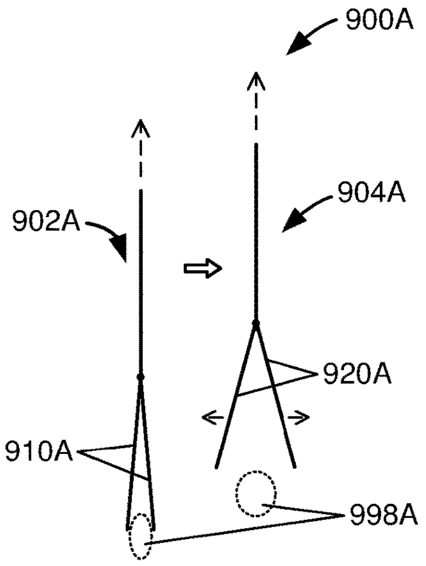
FIG. 9A schematically shows a retraction of an instrument that is initially in a grasping configuration, in accordance with one or more embodiments.

The flowchart of FIG. 6 describes a method for controlling instrument grip behavior when retracting an instrument with the instrument's jaws initially in a grasping configuration, in accordance with one or more embodiments. Some of the subsequently described steps are illustrated in FIG. 9A, showing a scenario (900A) involving the retraction of an instrument with the instrument's jaws initially in a grasping configuration. The method of FIG. 6 may be executed whenever an instrument is being withdrawn, or when an instrument is being withdrawn with the jaws of the instrument are initially in a grasping configuration. The retraction of an instrument may be performed in various ways. The retraction may be performed while the insertion degree of freedom is floating. The floating of the insertion degree of freedom (as described with reference to FIG. 3) may allow an operator to manually withdraw the instrument along the insertion axis of the instrument, e.g., by manually pulling on the carriage (described in FIG. 2) in a direction that approximately coincides with the insertion axis of the instrument.

Alternatively, the retraction may be actively performed by the manipulator assembly, by driving the joints of the manipulator assembly to move in a retraction direction, along the insertion axis of the instrument. The actively performed retraction may be performed in a supervised autonomous manner, in which a controller of the manipulator assembly controls the retraction while under human supervision. For example, the retraction of the instrument may be performed only while a user pushes a particular button and stops as soon as the button is released. The retraction may also be performed fully autonomously. Alternatively, the retraction may be teleoperated by a user at an input control device.

While FIG. 6 describes a coordination of instrument jaw movement with the movement of the instrument along the insertion axis, the jaw movement may be coupled to other instrument shaft degrees of freedom without departing from the disclosure.

Briefly summarized, the method of FIG. 6 causes the jaws of an instrument to target opening to a specified aperture, during retraction of the instrument. The opening of the jaws may help avoid an unintentional tugging on tissue that may be grasped by the jaws, when withdrawing the instrument. The details are subsequently provided.

Turning to the flowchart, in Step 600, the instrument movement is tracked along the instrument shaft degree of freedom. The instrument movement is tracked as the instrument may be moved, e.g., by an operator pushing or pulling along the instrument shaft degree of freedom while the instrument degree of freedom is floating, or while the manipulator assembly actively drives the instrument along the instrument shaft degree of freedom. The instrument shaft degree of freedom may be a movement along the insertion axis of the instrument, or any other instrument shaft degree of freedom. The obtained information about the instrument may be a current position and or a current velocity along the instrument shaft degree of freedom. The instrument movement may be tracked using sensory input from, for example, incremental encoders at the joints of the manipulator arm, allowing the movement along the instrument shaft degree of freedom to be reconstructed using forward kinematics.

In Step 610, a test is performed to determine whether a target aperture of the opening instrument jaws has been reached. The opening of the jaws may be performed as described in Step 620, and the current position of the jaws may be known, e.g., because the movement of the actuators causing the opening is tracked (using incremental encoder signals, for example). Once the target aperture of the opening instrument jaws has been reached, the execution of the method may terminate, and cease any further opening of the jaws. In this case, even though further opening of the jaws may have ceased, the retraction of the instrument may continue. If the target aperture of the opening instrument has not been reached, the method may proceed with the execution of Step 620. The target aperture of opening may be specified as an angle between the jaws, a distance between the jaws at the tip or an intermediate jaw location, an area spanned by the jaws, particular configurations of the jaws relative to each other or the shaft, etc. The target aperture of the opening instrument jaws may depend on various factors. These factors are discussed below, following the description of the flowcharts of FIG. 6, FIG. 7, and FIG. 8.

In Step 620, the size of the aperture defined by the jaws is coordinated with the movement of the instrument along the instrument shaft degree of freedom. The following steps may be performed:

In Step 622, a test is performed to determine whether the jaws are in a grasping configuration. The jaws may initially, at the beginning of the execution of the method of FIG. 6 be in the grasping configuration, but as the retraction of the instrument progresses, the jaws may no longer be in the grasping configuration. The grasping configuration may be achieved and maintained by the controller sending a control command causing the instrument jaws to exert a closing force. The closing force may be accomplished by overdriving the controller for the actuator(s) associated with the closing of the jaws. More specifically, the controller, for example, a PD controller, may be driven into saturation such that the actual position of the jaws can no longer reach the commanded position of the jaws, thereby causing the closing force. The closing force may exert pressure on an object that is being grasped, as illustrated in the left panel of FIG. 9A, described below. The presence of the grasping configuration may be detected in various ways. For example, the actual position of the jaws may be compared to the commanded position of the jaws. If a discrepancy beyond a preset threshold exists, the conclusion may be that the jaws are in a grasping configuration because the controller is driven into saturation. Alternatively, the actual position of the jaws itself may be used. For example, a grasping configuration may be detected based on the jaws being closed to at least a specified extent. Alternatively, the actual position of the instrument along the instrument shaft degree of freedom may be used. More specifically, initially, when the method of FIG. 6 is first executed, a grasping configuration is assumed to be present. As the instrument is retracted along the instrument shaft degree of freedom, after movement beyond a preset distance, the jaws may no longer be assumed to be in the grasping configuration, based on the opening of the jaws caused by the execution of Steps 624, 628, and 630.

If the jaws are determined to be in a grasping configuration, the method may proceed with the execution of Step 624. If the jaws are determined not to be in a grasping configuration, the method may proceed with the execution Step 624.

In Step 624, a higher gain for the coupling of the opening of the jaws to the retraction movement of the instrument is set. Specifically, the gain selected in Step 624 is higher in comparison to the gain, selected in Step 626. While the gain may be fixed, it may also be variable in a quantized or continuous manner. In one embodiment a continuous gain function rather than a constant gain, set of quantized gain values, or look-up table of gain values is used. For a given retraction rate, a higher gain may result in a faster opening of the yaws than a lower gain. The higher gain, when executing Steps 628 and 630, may cause a rapid relaxation of the jaws. More specifically, when the controller is initially driven into saturation to obtain a firm grasp, the higher gain may be selected such that a relatively small movement along the shaft degree of freedom reduces or eliminates the saturation. Accordingly, the jaws may still be in contact with the object, but may exert less force. A residual force may be a result of friction in the mechanical components of the jaws, actuators, etc. The rapid relaxation may reduce the likeliness of tugging on an object being grasped, during the retraction. Assume, for example, that in a surgical scenario, the forceps are used to hold a delicate blood vessel. It would be undesirable if the retraction of the instrument caused a significant pulling force on the blood vessel. Accordingly, the gain in Step 624 may be selected sufficiently high to allow relaxation of the jaws within no more than a few millimeters, e.g., 2-3 mm of instrument movement along the shaft degree of freedom. The rapid relaxation during the retraction may keep the blood vessel in contact with the jaws, but may allow it to slip as the retraction is continued.

In Step 626, a lower gain for the coupling of the opening of the jaws to the retraction movement of the instrument is set. Specifically, the gain selected in Step 626 is lower in comparison to the gain, selected in Step 624. The lower gain, when executing Steps 628 and 630, may cause a more gradual opening of the jaws relative to the retraction motion. The gain in Step 626 may be selected to cause a gradual opening of the jaws over a longer distance of instrument movement along the shaft degree of freedom, for example, multiple millimeters or centimeters. While the gain may be fixed, it may also be variable in a quantized or continuous manner. In one embodiment a continuous gain function rather than a constant gain, set of quantized gain values, or look-up table of gain values is used. If a function is used, the function gain in Step 626 may be lower than the function gain in Step 624.

While the setting of gains is described in Steps 624 and 628, those skilled in the art will appreciate that the gain used throughout the execution of the method of FIG. 6 are not necessarily constant. A variable gain may, for example, change in a position-dependent manner during the retraction motion. Any functions, e.g., monotonous functions that couple the jaw opening to the retraction motion may be used. In one or more embodiments, the functions are monotonous functions.

In Step 628, the gain set in Step 624 or in Step 626 is used to determine an actuator control command for the actuator(s) of the jaws. The actuator control command may be a position or velocity control command. The actuator control is set such that a jaw aperture, corresponding to the current position of the instrument along the shaft degree of freedom, as dictated by the gain, is obtained.

In Step 630, the actuator command is sent to the controller (s) of the jaw actuator(s) to cause the desired movement of the jaws. The opening of the jaws during the retraction of the instrument is illustrated in the right panel of FIG. 9A. In some embodiments where both jaws are moveable relative to the shaft, the movement of the jaws toward the target aperture may also involve repositioning or reshaping the jaw aperture. Repositioning or reshaping the jaw aperture may be by asymmetrically moving the jaws, moving one or more joints along the jaws for instruments with joints along the jaws, and the like. For example, a first jaw may be moved more relative to the shaft than a second jaw is moved relative to the shaft to reposition or reshape the jaw aperture.

In some embodiments where both jaws are moveable relative to the shaft, the opening or closing of the jaws toward the target aperture may also involve repositioning or reshaping the jaw aperture. Repositioning or reshaping the jaw aperture may be, by asymmetrically moving the jaws, moving one or more joints along the jaws for instruments with joints along the jaws, and the like. For example, a first jaw may be moved more relative to the shaft than a second jaw is moved relative to the shaft to reposition or reshape the jaw aperture.

Steps 600-630 may be repeated until the execution of the method terminates.

Figure 9B:
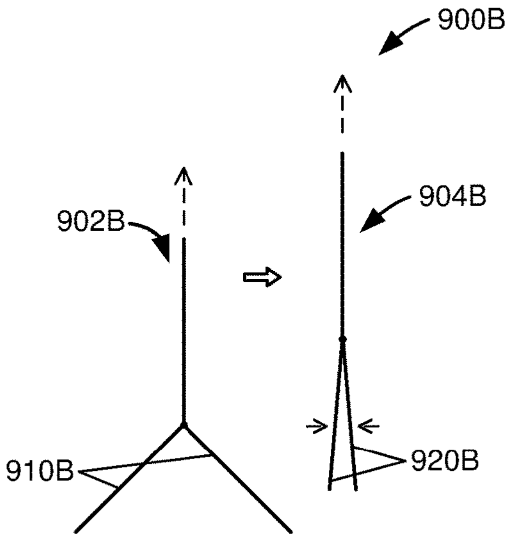
FIG. 9B schematically shows a retraction of an instrument that is initially in an open configuration, in accordance with one or more embodiments.
Figure 10A:
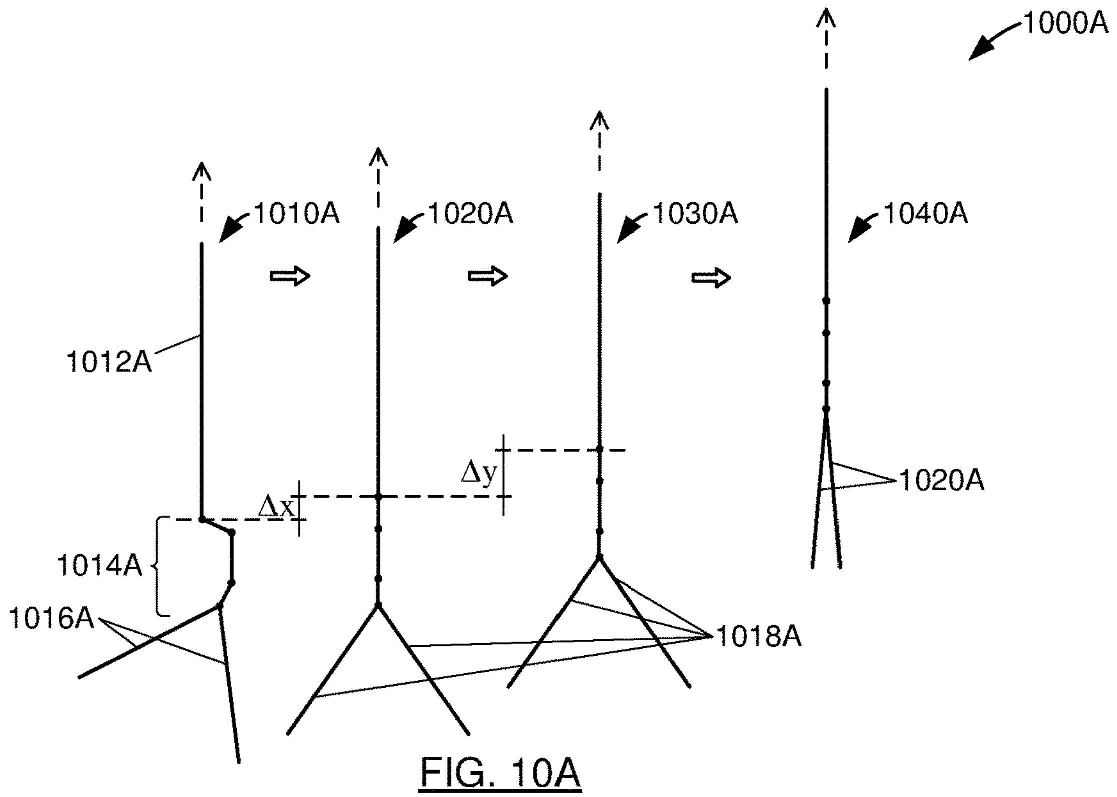
FIG. 10A schematically shows a sequence of configurations of an instrument being retracted, in accordance with one or more embodiments.
Figure 10B:
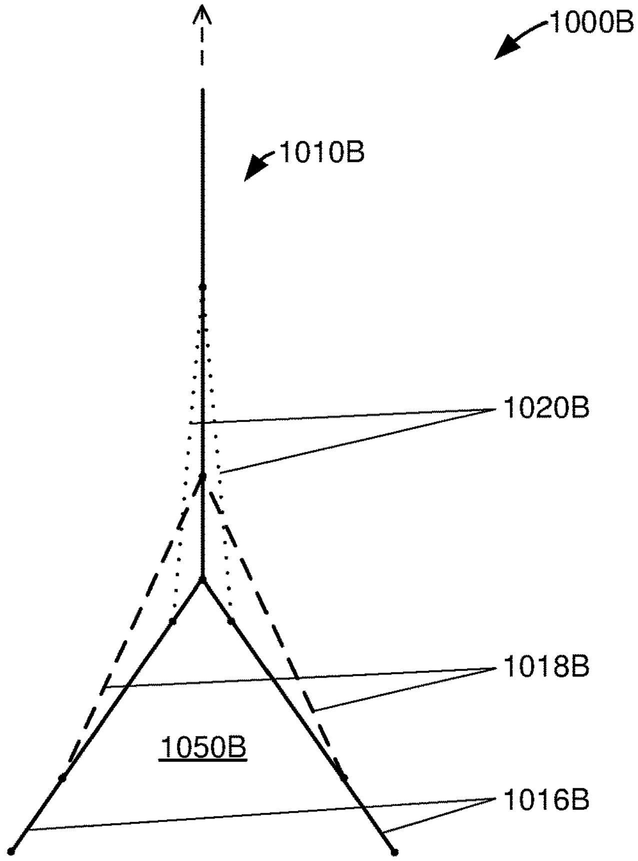
FIG. 10B schematically shows a sequence of configurations of an instrument being retracted, in accordance with one or more embodiments.

Turning to FIG. 7, the flowchart of FIG. 7 describes a method for controlling instrument grip behavior when retracting an instrument with the instrument's jaws initially in an open configuration, in accordance with one or more embodiments. The subsequently described steps are illustrated in FIG. 9B, showing a scenario (900B) involving the retraction of an instrument with the instrument's jaws initially in an open configuration, and in FIG. 10A and FIG. 10B illustrating additional scenarios, discussed below. As previously described, the retraction of an instrument may be performed in various ways. The retraction may be performed while the insertion degree of freedom is floating (as previously described with reference to FIG. 3). The floating of the insertion degree of freedom may allow an operator to manually withdraw the instrument along the insertion axis of the instrument, e.g., by manually pulling on the carriage (described in FIG. 2) in a direction that approximately coincides with the insertion axis of the instrument. Alternatively, the retraction may be actively performed by the manipulator assembly, by driving the joints of the manipulator assembly to move in a retraction direction, along the insertion axis of the instrument. The actively performed retraction may be performed in a supervised autonomous manner, in which a controller of the manipulator assembly controls the retraction while under human supervision. For example, the retraction of the instrument may be performed only while a user pushes a particular button and stops as soon as the button is released. The supervised autonomous retraction provides the user with control over the jaw movement through the driving of the instrument along the insertion degree of freedom (either actively by actuators or passively by back-driving by the user). When the user stops the back-driving, the jaws stop autonomously moving relative to the shaft. The retraction may also be performed fully autonomously. Alternatively, the retraction may be teleoperated by a user at an input control device. While FIG. 7 describes a coordination of instrument jaw movement with the movement of the instrument along the insertion axis, the jaw movement may be coupled to other instrument shaft degrees of freedom without departing from the disclosure.

Briefly summarized, the method of FIG. 7 causes the jaws of an instrument to target closing to a specified aperture, during retraction of the instrument. The closing of the jaws may help avoid contacting surrounding objects when retracting the instrument by reducing the profile of the jaws in the retraction direction: closed jaws during the insertion traverse a smaller volume in the workspace than open jaws, thereby reducing the risk of a collision. The details are subsequently provided.

Turning to the flowchart, in Step 700, the instrument movement is tracked along the instrument shaft degree of freedom. The instrument movement is tracked as the instrument may be moved, e.g., by an operator pushing or pulling along the instrument shaft degree of freedom while the instrument degree of freedom is floating, or while the manipulator assembly actively drives the instrument along the instrument shaft degree of freedom. The instrument shaft degree of freedom may be a movement along the insertion axis of the instrument, or any other instrument shaft degree of freedom. The obtained information about the instrument may be a current position and or a current velocity along the instrument shaft degree of freedom. The instrument movement may be tracked using sensory input from, for example, incremental encoders at the joints of the manipulator arm, allowing the movement along the instrument shaft degree of freedom to be reconstructed using forward kinematics.

In Step 710, a test is performed to determine whether a target aperture of the closing instrument jaws has been reached. The closing of the jaws may be performed as described in Step 720, and the current position of the jaws may be known, e.g., because the movement of the actuators causing the closing is tracked (using incremental encoder signals, for example). Once the target aperture of the closing instrument jaws has been reached, the execution of the method may terminate to cease the closing of the jaws. In this case, even though the closing of the jaws may have ceased, the retraction of the instrument may continue. If the target aperture of the closing instrument has not been reached, the method may proceed with the execution of Step 720. The target aperture of closing may be specified as an angle. The target aperture of closing may correspond to partially closed or completely closed instrument jaws. The target aperture of closing may depend on various factors. These factors are discussed below, following the description of the flowcharts of FIG. 6, FIG. 7, and FIG. 8.

In Step 720, the size of the aperture defined by the jaws is coordinated with the movement of the instrument along the instrument shaft degree of freedom. The following steps may be performed:

In Step 722, one or more of the instrument joints are straightened. As illustrated in FIG. 10A, an instrument may have multiple joints along the instrument shaft to enhance the ability to articulate the instrument. As the instrument shaft is retracted, the one or more joints may be straightened, as shown in the first and second panel (from the left), in FIG. 10A. The instrument jaws may be kept in the open configuration, during the execution of Step 722. Execution of Step 722 is optional.

In Step 724, the instrument jaws are kept in the open position, while the instrument is retracted over a short distance along the instrument shaft degree of freedom. The retraction over a short distance while keeping the instrument jaws open may allow squishy or elastic objects that may initially be in contact with the instrument jaws to relax or expand. Inadvertent grasping of such objects may, thus, be avoided. The retraction of the instrument in Step 724 may be limited to a few millimeters. Execution of Step 724 is optional.

In Step 726, a gain for the coupling of the closing of the jaws to the retraction movement of the instrument is set. The gain, when executing Steps 728 and 730, may cause a gradual opening of the jaws. The gain in Step 726 may be selected to cause a gradual opening of the jaws over a longer distance of instrument movement along the shaft degree of freedom, for example, multiple millimeters or centimeters. Those skilled in the art will appreciate that the gain used throughout the execution of the method of FIG. 7 is not necessarily constant. A variable gain may, for example, change in a position-dependent manner during the retraction motion. Any function, linear or non-linear, may be used. In one embodiment, the function is a monotonic function. In another embodiment, the function is a non-monotonic function. Execution of Step 726 is optional; for example, if the gain is preset or "hard-wired," then no need exists to set the gain again.

In one embodiment, the gain is set such that it prevents the jaws from entering a keep-out zone during the retraction, as illustrated in FIG. 10B. The keep-out zone defines a region enclosed by the jaws when in the initial open configuration. A rapid closure of the jaws, cause by a high gain, would cause the jaws to enter the keep-out zone, thereby potentially coming in contact with an object located in the keep out zone. By selecting a gain that is low enough to avoid entering the keep-out zone, the closing jaws may avoid the object. A detailed description is provided below with reference to FIG. 10B.

In Step 728, the gain set in Step 726 is used to determine an actuator control command for the actuator(s) of the jaws. The actuator control command may be a position or velocity control command. The actuator control is set such that a jaw aperture of closing, corresponding to the current position of the instrument along the shaft degree of freedom, as dictated by the gain, is obtained.

In Step 730, the actuator command is sent to the controller(s) of the jaw actuator(s) to cause the desired movement of the jaws. The resulting closing of the jaws during the retraction of the instrument is illustrated in the right panel of FIG. 9B. In some embodiments where both jaws are moveable relative to the shaft, the movement of the jaws toward the target aperture may also involve repositioning or reshaping the jaw aperture. Repositioning or reshaping the jaw aperture may be by asymmetrically moving the jaws, moving one or more joints along the jaws for instruments with joints along the jaws, and the like. For example, a first jaw may be moved more relative to the shaft than a second jaw is moved relative to the shaft to reposition or reshape the jaw aperture.

Steps 700-730 may be repeated until the execution of the method terminates.

Figure 9C:
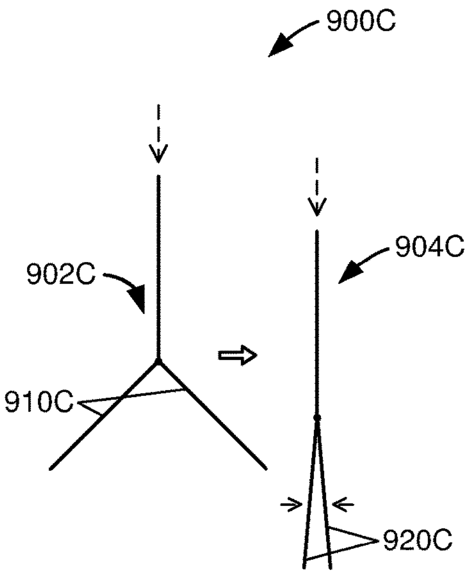
FIG. 9C schematically shows an insertion of an instrument that is initially in an open configuration, in accordance with one or more embodiments.

The flowchart of FIG. 8 describes a method for controlling instrument grip behavior when inserting an instrument with the instrument's jaws initially in an open configuration, in accordance with one or more embodiments. The subsequently described steps are illustrated in FIG. 9C, showing a scenario (900C) involving the insertion of an instrument with the instrument's jaws initially in an open configuration. The insertion of an instrument may be performed in various ways. The insertion may be performed while the insertion degree of freedom is floating (as previously described with reference to FIG. 3). The floating of the insertion degree of freedom may allow an operator to manually insert the instrument along the insertion axis of the instrument, e.g., by manually pushing the carriage (described in FIG. 2) in a direction that approximately coincides with the insertion axis of the instrument. Alternatively, the retraction may be actively performed by the manipulator assembly, by driving the joints of the manipulator assembly to move in an insertion direction, along the insertion axis of the instrument. The actively performed insertion may be performed in a supervised autonomous manner, in which a controller of the manipulator assembly controls the retraction while under human supervision. For example, the insertion of the instrument may be performed only while a user pushes a particular button, and stops as soon as the button is released. The supervised autonomous insertion provides the user with control over the jaw movement through the driving of the instrument along the insertion degree of freedom (either actively by actuators or passively by back-driving by the user). When the user stops the back-driving, the jaws stop autonomously moving relative to the shaft. The insertion may also be performed fully autonomously. Alternatively, the insertion may be teleoperated by a user at an input control device. While FIG. 8 describes a coordination of instrument jaw movement with the movement of the instrument along the insertion axis, the jaw movement may be coupled to other instrument shaft degrees of freedom without departing from the disclosure.

Briefly summarized, the method of FIG. 8 causes the jaws of an instrument to target closing to a specified extent, during insertion of the instrument. The closing of the jaws may help avoid contacting surrounding objects when inserting the instrument by reducing the profile of the jaws in the insertion direction: for most instruments, closed jaws during the insertion presents a smaller cross-section in the insertion direction than open jaws, thereby reducing the risk of a collision. The details are subsequently provided.

Turning to the flowchart, in Step 800, the instrument movement is tracked along the instrument shaft degree of freedom. The instrument movement is tracked as the instrument may be moved, e.g., by an operator pushing or pulling along the instrument shaft degree of freedom while the instrument degree of freedom is floating, or while the manipulator assembly actively drives the instrument along the instrument shaft degree of freedom. The instrument shaft degree of freedom may be a movement along the insertion axis of the instrument, or any other instrument shaft degree of freedom. The obtained information about the instrument may be a current position and or a current velocity along the instrument shaft degree of freedom. The instrument movement may be tracked using sensory input from, for example, incremental encodes at the joints of the manipulator arm, allowing the movement to be reconstructed using forward kinematics.

In Step 810, a test is performed to determine whether a target aperture of the closing instrument jaws has been reached. The closing of the jaws may be performed as described in Step 820, and the current position of the jaws may be known, e.g., because the movement of the actuators causing the closing is tracked (using incremental encoder signals, for example). Once the target aperture of the closing instrument jaws has been reached, the execution of the method may terminate to cease the closing of the jaws. In this case, even though the closing of the jaws may have ceased, the retraction of the instrument may continue. If the target aperture of closing the instrument jaws has not been reached, the method may proceed with the execution of Step 820. The target aperture of closing may be specified as an angle. The target aperture of closing may depend on various factors. These factors are discussed below, following the description of the flowcharts of FIGS. 6, 7, and 8.

In Step 820, the size of the aperture defined by the jaws is coordinated with the movement of the instrument along the instrument shaft degree of freedom. The following steps may be performed:

In Step 822, a gain for the coupling of the closing of the jaws to the insertion movement of the instrument is set. The gain may be selected to cause a gradual closing of the jaws over a longer distance of instrument movement along the shaft degree of freedom, for example, multiple millimeters or centimeters. Those skilled in the art will appreciate that the gain used throughout the execution of the method of FIG. 8 is not necessarily constant. A variable gain may, for example, change in a position-dependent manner during the insertion motion. Any function, linear or non-linear, may be used. In one embodiment, the function is a monotonic function. In another embodiment, the function is a non-monotonic function.

In Step 824, the gain set in Step 822 is used to determine an actuator control command for the actuator(s) of the jaws. The actuator control command may be a position or velocity control command. The actuator control is set such that a jaw aperture of closing, corresponding to the current position of the instrument along the shaft degree of freedom, as dictated by the gain, is obtained.

In Step 826, the actuator command is sent to the controller (s) of the jaw actuator(s) to cause the desired movement of the jaws. The resulting closing of the jaws during the insertion of the instrument is illustrated in the right panel of FIG. 9C. In some embodiments where both jaws are moveable relative to the shaft, the movement of the jaws toward the target aperture may also involve repositioning or reshaping the jaw aperture. Repositioning or reshaping the jaw aperture may be by asymmetrically moving the jaws, moving one or more joints along the jaws for instruments with joints along the jaws, and the like. For example, a first jaw may be moved more relative to the shaft than a second jaw is moved relative to the shaft to reposition or reshape the jaw aperture.

Steps 800-826 may be repeated until the execution of the method terminates.

While the flowcharts of FIG. 6, FIG. 7, and FIG. 8 describe the control of instrument grip behavior during an insertion or a retraction of an instrument, additional variations of these methods may exist, including those described below.

In one or more embodiments, the coordination of the size of the aperture defined by the jaws with the movement of the instrument along the instrument shaft degree of freedom is unidirectional. Specifically, for example, in the method of FIG. 6, a retraction may cause an opening of the instrument jaws, and reversal of the movement results in a closing of the instrument jaws that mirrors partially or entirely the closing of the instrument jaws. As another specific example, in the method of FIG. 6, a retraction may cause an opening of the instrument jaws, but reversal of the movement direction (resulting in an insertion) does not result in an opening or closing of the jaws (i.e., instead maintaining the current jaw configuration in a ratcheting-type response). Similarly, in the method of FIG. 7, a retraction may cause a closing of the instrument jaws, but reversal of the movement direction (resulting in an insertion) results in an opening of the instrument jaws that mirrors partially or entirely the closing of the instrument jaws, or (in a ratcheting-type response) does not result in an opening of the jaws. Also, in FIG. 8, an insertion may cause a closing of the instrument jaws, but reversal of the movement direction (resulting in a retraction) results in an opening of the instrument jaws that mirrors partially or entirely the closing of the instrument jaws, or (in a ratcheting-type response) does not result in an opening of the jaws. In one or more embodiments, the ratcheting-type responses support an insertion/retraction using a ratcheting approach. Using the ratcheting approach, a user may repeatedly perform multiple alternating short insertion/retraction movements to cause a stepwise opening/closing of the yaws, based on the described unidirectional implementation. The ratcheting may provide the user with superior control over the insertion/retraction, in comparison to an insertion/retraction that is performed in a single stroke. One particular application of the ratcheting approach is the insertion of an instrument into a narrow diameter opening. By performing small, repeated insertion and retraction strokes, the user may gradually close the yaws to fit through the narrow diameter opening in a controlled manner.

In one or more embodiments, the target aperture, i.e., the extent of jaw opening/closing (as used in Steps 610, 710, and 810) may be set based on various considerations including mechanical constraints, the risk associated with the current task, the type of instrument being used, etc. For example, an unintended touch of an object may be considered more problematic within the workspace, in comparison to an unintended touch in the external environment. Accordingly, the target aperture of jaw opening/closing inside the workspace may be biased toward a more closed jaw configuration, compared to the target aperture that would be used in the external environment. Additional considerations may apply. For example, the target aperture of jaw closing may be dictated by requirements such as a diameter of an access port, a cannula, or any other structure through which the instrument jaws may need to pass. Further, the target aperture of jaw opening/closing may also be instrument specific: In case of a clip applier, it may be desirable to keep the jaws of the clip applier in a more open configuration to avoid an inadvertent operation of the clip applier. In case of scissors, it may be desirable to keep the jaws (i.e., the blades) in a more closed configuration to reduce blade exposure. Alternatively, a fixed angle may be specified for the target aperture. A target aperture may further depend on the position of the instrument on the insertion axis. Discrete values may be set for different positions. Alternatively, a function, linear or non-linear, may establish the target aperture in a position-dependent manner. Also, setting the target aperture may be directional to obtain a hysteresis. More specifically, when moving from a more open to a more closed aperture, the target aperture may be chosen to be narrower than when moving from a more closed to a more open aperture. For example, the target aperture for closing the jaws may be set to 20°, whereas the target aperture for opening the jaws may be set to 30°. The difference between the target apertures may be selected such that it compensates for a backlash in the drivetrain of the instrument. If properly selected, the actual aperture of the jaws for opening and closing may be identical or near-identical despite the backlash, when commanding the target apertures specific to opening and closing, respectively.

Turning to FIG. 9A, FIG. 9B, FIG. 9C, and FIG. 9D retractions/insertions of instruments for various configurations of the instruments are shown to further illustrate the execution of the methods of FIG. 6, FIG. 7, and FIG. 8.

FIG. 9A schematically shows a scenario (900A) in which an instrument (902A, 904A) is retracted when initially in a grasping configuration, in accordance with one or more embodiments. The coordination of the instrument jaws (910A, 920A) during the retraction may be performed as described in FIG. 6. The left panel of FIG. 9A shows the instrument (902A) prior to the retraction. The jaws (910A) are grasping an object (998A). The retraction of the instrument (904A) causes a rapid relaxation of the instrument jaws, followed by a more gradual opening of the instrument jaws (920A), as shown in the right panel of FIG. 9A. Due to the initial rapid relaxation, the retraction is performed without exposing the object (998A) to significant tugging forces.

FIG. 9B schematically shows a scenario (900B) in which an instrument (902B, 904B) is retracted when initially in an open configuration, in accordance with one or more embodiments. The coordination of the instrument jaws (910B, 920B) during the retraction may be performed as described in FIG. 7. The left panel of FIG. 9B shows the instrument (902B) prior to the retraction. The jaws (910B) are in an open configuration. The retraction of the instrument (904B) causes a gradual closing of the instrument jaws (920B), as shown in the right panel of FIG. 9B. By closing the jaws (910B) during the retraction, the likeliness of unintended interaction of the instrument (904B) with objects in the surrounding environment is reduced.

FIG. 9C schematically shows a scenario (900C) in which an instrument (902C, 904C) is inserted when initially in an open configuration, in accordance with one or more embodiments. The coordination of the instrument jaws (910C, 920C) during the insertion may be performed as described in FIG. 8. The left panel of FIG. 9C shows the instrument (902C) prior to the insertion. The jaws (910C) are in an open configuration. The insertion of the instrument (904C) causes a gradual closing of the instrument jaws (920C), as shown in the right panel of FIG. 9C. By closing the jaws (910C) during the insertion, the likeliness of unintended interaction of the instrument (904C) with objects in the surrounding environment is reduced.

Figure 9D:
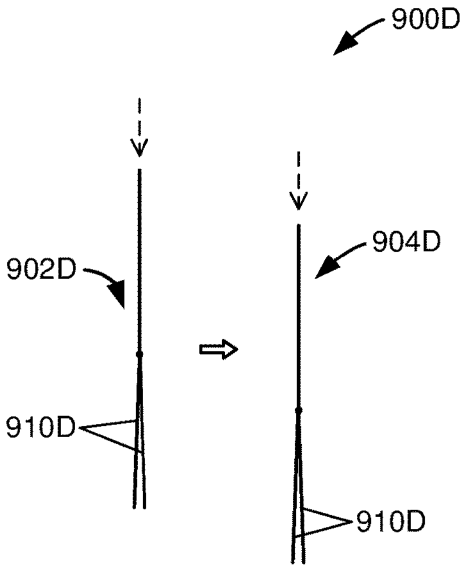
FIG. 9D schematically shows an insertion of an instrument that is initially in a closed configuration, in accordance with one or more embodiments.

FIG. 9D schematically shows a scenario (900D) in which an instrument (902D, 904D) is inserted when initially in a substantially closed configuration, in accordance with one or more embodiments. The instrument jaws (910D) may be held at a constant angle, during the insertion. The left panel of FIG. 9D shows the instrument (902D) prior to the insertion. The jaws (910D) are in a substantially closed configuration and remain in the substantially closed configuration during the insertion of the instrument (904D), as shown in the right panel of FIG. 9D. By holding the jaws (910D) in a substantially closed configuration, the likeliness of unintended interaction of the instrument (904D) with objects in the surrounding environment is reduced.

Turning to FIG. 10A, a scenario (1000A) including a sequence of configurations of an instrument being retracted, in accordance with one or more embodiments, is shown. FIG. 10A illustrates some of the steps of the flowchart of FIG. 7. Initially (first panel from the left) a set of articulated instrument joints (1014A) along the instrument shaft (1012A) are articulated. The jaws (1016A) are in an open configuration and oriented based on the articulation of the instrument joints (1014A). As described in Step 722 of the method of FIG. 7, when the retraction of the instrument begins, the instrument joints are straightened, resulting in the configuration shown in the second panel from the left. Here, the instrument joints, after retraction of the instrument (1020A) over a short distance Δx, are no longer articulated. The jaws (1018A) remain in the open configuration, but the orientation of the jaws has changed, as a result of the straightening of the instrument joints. The third panel from the left shows the instrument (1030A) after an additional retraction over a short distance Δy. The jaws (1018A) have been retracted, while keeping the instrument jaws open. The fourth (rightmost) panel shows the instrument (1040A) after a continued retraction which has caused the instrument jaws (1020A) to close. The incremental retraction of the instrument without immediately beginning to close the jaws may allow squishy or elastic objects that may initially be in contact with the instrument jaws to relax or expand. An inadvertent grasping of such objects may, thus, be avoided. The straightened instrument may then be retracted while reducing the likeliness of interaction with other surrounding objects.

Turning to FIG. 10B, a scenario (1000B) including a sequence of configurations of an instrument being retracted, in accordance with one or more embodiments, is shown. FIG. 10B illustrates some of the steps of the flowchart of FIG. 7. Initially (instrument shown using solid line style) the jaws (1016B) of the instrument (1010B) are in an open configuration. Throughout the execution of Steps 726-730 of FIG. 7, the instrument jaws gradually close. FIG. 10B shows the instrument jaws (1018B) in an intermediate position (dashed line style) and in a nearly closed position (dotted line style). During the retraction of the instrument (1010B), the instrument jaws (1016B, 1018B, 1020B) strictly remain outside a keep-out zone (1050B). In FIG. 10B, the keep-out zone (1050B) is the region delimited by the jaws (1016B) in the initial open configuration. By avoiding the keep-out zone (1050B) during the closing of the jaws, it may be ensured that the jaws do not inadvertently interfere with an object that may be located in the keep-out zone (1050B). To avoid the keep-out zone (1050B) during retraction of the instrument (1010B), the gain coupling jaw closing to instrument retraction may be set sufficiently small to ensure a gradual closing of the jaws, when executing Step 726 of the flowchart. In the example provided in FIG. 10B, the gain is continuously modulated to keep the tips of the jaws on the geometry of the jaws in the initially open position. The geometry of the jaws may be, for example, a centerline of the jaws, a volume of the jaws, etc.

What is claimed is:

1. A computer-assisted medical system comprising:

a robotic manipulator arm configured to support an instrument, the instrument comprising an instrument shaft, and jaws disposed at a distal end of the instrument shaft; and a controller coupled to the manipulator arm, the controller comprising a computer processor and configured to:

track a movement of the instrument along an insertion axis of the instrument wherein the movement of the instrument comprises a retraction of the instrument, and actuate the jaws to coordinate a size of a jaw aperture defined by the jaws with the movement of the instrument along the insertion axis to reach a target aperture, wherein coordinating the size of the jaw aperture defined by the jaws comprises:

(i) rapidly relaxing the jaws during a first phase of the retraction, and opening the jaws toward the target aperture during a second phase of the retraction; or (ii) closing, during the retraction and in response to the jaws being in an initially open configuration at a beginning of the retraction, the jaws from the initially open configuration toward the target aperture while keeping the jaws out of a keep-out zone.

2. The computer-assisted medical system of claim 1, wherein the size of the jaw aperture is coupled to the movement of the instrument along the insertion axis by a function set by the controller.

3. The computer-assisted medical system of claim 1, wherein coordinating the size of the jaw aperture defined by the jaws comprises: controlling the size of the jaw aperture defined by the jaws until the target aperture is reached.

4. The computer-assisted medical system of claim 1, wherein coordinating the size of the jaw aperture defined by the jaws further comprises:

in response to the jaws being in an initially grasping configuration, opening the jaws from the initially grasping configuration toward the target aperture as the instrument is retracted, and closing the jaws as the instrument is inserted after having been retracted.

5. The computer-assisted medical system of claim 1, wherein coordinating the size of the jaw aperture defined by the jaws comprises: the closing the jaws from the initially open configuration toward the target aperture while keeping the jaws out of the keep-out zone; and wherein coordinating the size of the jaw aperture defined by the jaws further comprises: opening the jaws as the instrument is inserted after having been retracted.

6. The computer-assisted medical system of claim 1, wherein coordinating the size of the jaw aperture defined by the jaws further comprises: maintaining the size of the jaw aperture defined by the jaws as the instrument is inserted after having been retracted.

7. The computer-assisted medical system of claim 1, wherein coordinating the size of the jaw aperture defined by the jaws comprises: the rapidly relaxing the jaws during the first phase and opening the jaws toward the target aperture during the second phase, wherein the size of the jaw aperture is coupled to the movement of the instrument along the insertion axis by a gain factor set by the controller, and wherein the controller causes the rapid relaxation of the jaws by setting the gain factor to a first value, and wherein the controller causes the opening of the jaws by setting the gain factor to a second value lower than the first value.

8. The computer-assisted medical system of claim 1, wherein the keep-out zone is a region enclosed by the jaws in the initially open configuration.

9. The computer-assisted medical system of claim 1, wherein coordinating the size of the jaw aperture defined by the jaws during the retraction to keep the jaws out of the keep-out zone further comprises: controlling the jaws during the retraction such that tips of the jaws follow a geometry of the jaws in the initially open configuration.

10. The computer-assisted medical system of claim 1, wherein coordinating the size of the jaw aperture defined by the jaws comprises: the closing the jaws from the initially open configuration toward the target aperture; and wherein the controller is further configured to: prior to closing the jaws from the initially open configuration, straighten at least one joint of the instrument, the at least one joint of the instrument located proximal to the jaws.

11. The computer-assisted medical system of claim 10, wherein the controller is further configured to, prior to closing the jaws from the initially open configuration and after straightening the at least one joint, maintain the jaws in the initially open configuration.

12. The computer-assisted medical system of claim 1, wherein coordinating the size of the jaw aperture defined by the jaws further comprises:

in response to the movement of the instrument comprising an insertion of the instrument with the jaws in an initially open configuration, closing the jaws toward a target closing.

13. The computer-assisted medical system of claim 1, wherein the target aperture is a first target aperture in response to at least a portion the jaws being on a first side of a physical boundary, wherein the target aperture is a second target aperture in response to the at least a portion of the jaws being on a second side of the physical boundary, and wherein the first target aperture differs from the second target aperture.

14. The computer-assisted medical system of claim 1, wherein the computer processor is further configured to coordinate the size of the jaw aperture using a ratcheting approach by alternatingly:

changing the size of the jaw aperture for the movement of the instrument in a first direction, and holding constant the size of the jaw aperture for the movement of the instrument in a second direction opposing the first direction.

15. The computer-assisted medical system of claim 1, wherein the target aperture is set based on at least one risk selected from the group consisting of:

a risk associated with the instrument, and a risk associated with a task currently being performed using the computer-assisted medical system.

16. A method for operating a medical system, comprising:

tracking a movement of an instrument along an insertion axis of the instrument, wherein the movement of the instrument comprises a retraction of the instrument, and wherein the instrument comprises an instrument shaft and jaws disposed at a distal end of the instrument shaft; and actuating the jaws to coordinate a size of a jaw aperture defined by the jaws with the movement of the instrument along the insertion axis to reach a target aperture, wherein coordinating the size of the jaw aperture defined by the jaws comprises:

(i) rapidly relaxing the jaws during a first phase of the retraction, and opening the jaws toward the target aperture during a second phase of the retraction, or (ii) closing, during the retraction and in response to the jaws being in an initially open configuration at a beginning of the retraction, the jaws from the initially open configuration toward the target aperture while keeping the jaws out of a keep-out zone.

17. The method of claim 16, wherein coordinating the size of the jaw aperture defined by the jaws further comprises:

maintaining the size of the jaw aperture defined by the jaws as the instrument is inserted after having been retracted; or in response to the movement of the instrument comprising an insertion of the instrument with the jaws in an initially open configuration, closing the jaws toward a target closing.

18. The method of claim 16, wherein the keep-out zone is a region enclosed by the jaws in the initially open configuration.

19. The method of claim 16, wherein coordinating the size of the jaw aperture defined by the jaws comprises: the closing the jaws from the initially open configuration toward the target aperture, and wherein the method further comprises: prior to closing the jaws from the initially open configuration, straightening at least one joint of the instrument, the at least one joint of the instrument located proximal to the jaws.

20. The method of claim 16, wherein the target aperture is based on whether a portion the jaws being on a first side or a second side of a physical boundary, the physical boundary separating a worksite from an external environment; or wherein the target aperture is based on at least one risk selected from the group consisting of: a risk associated with the instrument, and a risk associated with a task currently being performed using the medical system.

21. The method of claim 16, further comprising coordinating the size of the jaw aperture using a ratcheting approach by alternatingly:

changing the size of the jaw aperture for the movement of the instrument in a first direction, and holding constant the size of the jaw aperture for the movement of the instrument in a second direction opposing the first direction.

22. The method of claim 16, wherein coordinating the size of the jaw aperture defined by the jaws during the retraction to keep the jaws out of the keep-out zone further comprises: controlling the jaws during the retraction such that tips of the jaws follow a geometry of the jaws in the initially open configuration.

23. A non-transitory machine-readable medium comprising a plurality of machine-readable instructions executed by one or more processors associated with a medical system, the plurality of machine-readable instructions causing the one or more processors to perform a method comprising:

tracking a movement of an instrument along an insertion axis of the instrument, wherein the movement of the instrument comprises a retraction of the instrument, and wherein the instrument comprises an instrument shaft and jaws disposed at a distal end of the instrument shaft; and actuating the jaws to coordinate a size of a jaw aperture defined by the jaws with the movement of the instrument along the insertion axis to reach a target aperture, wherein coordinating the size of the jaw aperture defined by the jaws comprises:

(i) rapidly relaxing the jaws during a first phase of the retraction, and opening the jaws toward the target aperture during a second phase of the retraction, or (ii) closing, during the retraction and in response to the jaws being in an initially open configuration at a beginning of the retraction, the jaws from the initially open configuration toward the target aperture while keeping the jaws out of a keep-out zone.

24. The non-transitory machine-readable medium of claim 23, wherein coordinating the size of the jaw aperture defined by the jaws further comprises:

maintaining the size of the jaw aperture defined by the jaws as the instrument is inserted after having been retracted; or closing the jaws toward a target closing in response to the movement of the instrument comprising an insertion of the instrument with the jaws in an initially open configuration; or changing the size of the jaw aperture for the movement of the instrument in a first direction and holding constant the size of the jaw aperture for the movement of the instrument in a second direction, the second direction opposing the first direction.

25. The non-transitory machine-readable medium of claim 23, wherein the target aperture is set based on whether a portion the jaws is on a first side or a second side of a physical boundary, the physical boundary separating a worksite from an external environment; or wherein the target aperture is based on at least one risk selected from the group consisting of: a risk associated with the instrument, and a risk associated with a task currently being performed using the medical system.

26. The non-transitory machine-readable medium of claim 23, wherein the keep-out zone is a region enclosed by the jaws in the initially open configuration.

27. The non-transitory machine-readable medium of claim 23, wherein coordinating the size of the jaw aperture defined by the jaws comprises: the closing the jaws from the initially open configuration toward the target aperture as the instrument is retracted, and wherein the method further comprises: prior to closing the jaws from the initially open configuration, straightening at least one joint of the instrument, the at least one joint of the instrument located proximal to the jaws.

28. The non-transitory machine-readable medium of claim 23, wherein coordinating the size of the jaw aperture defined by the jaws during the retraction to keep the jaws out of the keep-out zone further comprises: controlling the jaws during the retraction such that tips of the jaws follow a geometry of the jaws in the initially open configuration.

* * * * *